United States Patent
Powell et al.

(10) Patent No.: US 9,242,913 B2
(45) Date of Patent: Jan. 26, 2016

(54) METHODS AND SYSTEMS EMPLOYING A HORIZONTALLY CONFIGURED DIGESTION UNIT FOR HYDROTHERMAL DIGESTION OF CELLULOSIC BIOMASS SOLIDS

(71) Applicant: SHELL OIL COMPANY, Houston, TX (US)

(72) Inventors: Joseph Broun Powell, Houston, TX (US); Alouisius Nicolaas Renee Bos, Amsterdam (NL); Peter Anton August Klusener, Amsterdam (NL); Ingmar Hubertus Josephina Ploemen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/264,724

(22) Filed: Apr. 29, 2014

(65) Prior Publication Data

US 2014/0330049 A1 Nov. 6, 2014

Related U.S. Application Data

(60) Provisional application No. 61/817,996, filed on May 1, 2013.

(51) Int. Cl.
| | |
|---|---|
| *C07C 29/132* | (2006.01) |
| *C08H 8/00* | (2010.01) |
| *C08H 7/00* | (2011.01) |
| *C10G 1/06* | (2006.01) |
| *C10G 1/08* | (2006.01) |
| *C10G 3/00* | (2006.01) |
| *C10G 1/00* | (2006.01) |

(52) U.S. Cl.
CPC ............... *C07C 29/132* (2013.01); *C08H 6/00* (2013.01); *C08H 8/00* (2013.01); *C10G 1/002* (2013.01); *C10G 1/006* (2013.01); *C10G 1/065* (2013.01); *C10G 1/08* (2013.01); *C10G 1/083* (2013.01); *C10G 3/42* (2013.01); *C10G 3/46* (2013.01); *C10G 3/48* (2013.01); *C10G 3/50* (2013.01); *C10G 3/55* (2013.01); *C10G 2300/1014* (2013.01); *Y02E 50/343* (2013.01)

(58) Field of Classification Search
None
See application file for complete search history.

(56) References Cited

U.S. PATENT DOCUMENTS

| | | |
|---|---|---|
| 2,966,215 A | 12/1960 | Durkee |
| 6,030,915 A | 2/2000 | De Boer |
| 6,127,299 A | 10/2000 | De Boer et al. |
| 2010/0236988 A1 | 9/2010 | Gabrielov et al. |
| 2011/0120663 A1 | 5/2011 | Engstrom et al. |
| 2012/0317872 A1 | 12/2012 | Powell et al. |
| 2013/0109896 A1 | 5/2013 | Powell et al. |
| 2013/0152457 A1 | 6/2013 | Powell et al. |
| 2013/0152458 A1 | 6/2013 | Powell et al. |
| 2014/0000153 A1 | 1/2014 | Powell |
| 2014/0005444 A1 | 1/2014 | Komplin et al. |
| 2014/0005445 A1 | 1/2014 | Komplin et al. |

FOREIGN PATENT DOCUMENTS

| | | |
|---|---|---|
| EP | 344462 | 12/1989 |
| WO | 9105907 | 5/1991 |

OTHER PUBLICATIONS

International Search Report dated Oct. 31, 2014 of PCT/US2014/035863 filed Apr. 29, 2014.

*Primary Examiner* — Brian J Davis

(57) ABSTRACT

Biomass compaction during hydrothermal digestion of cellulosic biomass solids may become problematic, particularly as the vertical height of a cellulosic biomass charge increases. Compaction may be decreased in a horizontally configured hydrothermal digestion unit. Methods for digesting cellulosic biomass solids may comprise: providing a hydrothermal digestion unit having a length or a width greater than its height and containing a fluid phase digestion medium and a slurry catalyst capable of activating molecular hydrogen; introducing cellulosic biomass solids to the hydrothermal digestion unit; distributing the cellulosic biomass solids laterally within the hydrothermal digestion unit; after or while the cellulosic biomass solids are being distributed, supplying an upwardly directed flow of molecular hydrogen through the cellulosic biomass solids and the fluid phase digestion medium; and heating the cellulosic biomass solids in the presence of the slurry catalyst and the molecular hydrogen, thereby forming an alcoholic component derived from the cellulosic biomass solids.

33 Claims, 12 Drawing Sheets

METHODS AND SYSTEMS EMPLOYING A HORIZONTALLY CONFIGURED DIGESTION UNIT FOR HYDROTHERMAL DIGESTION OF CELLULOSIC BIOMASS SOLIDS

The present application claims the benefit of U.S. Provisional Patent Application Ser. No. 61/817,996, filed May 1, 2013, the entire disclosure of which is hereby incorporated by reference.

TECHNICAL FIELD OF THE INVENTION

The present disclosure generally relates to digestion of cellulosic biomass solids, and, more specifically, to systems and methods in which cellulosic biomass solids may be processed in a hydrothermal digestion unit having a length and/or a width that is greater than its height.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). Moreover, conventional bio-based processes have typically produced intermediates in dilute aqueous solutions (>50% water by weight) that are difficult to further process. Energy- and cost-efficient processes for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from cellulosic biomass may be converted into a more usable form. However, fermentation processes are typically slow, require large volume reactors and high dilution conditions, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner. Paper and pulpwood digestion processes also typically remove lignin from the raw cellulosic biomass prior to pulp formation. Although digestion processes used in connection with forming fuel blends and other materials may likewise remove lignin prior to digestion, these extra process steps may impact the energy efficiency and cost of the biomass conversion process. The presence of lignin during high-conversion cellulosic biomass digestion may be particularly problematic in some instances.

Production of soluble carbohydrates for use in fuel blends and other materials via routine modification of paper and pulpwood digestion processes is not believed to be economically feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Depending on the reaction conditions and catalyst used, reaction products formed as a result of conducting one or more catalytic reduction reactions on soluble carbohydrates may comprise one or more alcohol functional groups, particularly including triols, diols, monohydric alcohols, and any combination thereof, some of which may also include a residual carbonyl functionality (e.g., an aldehyde or a ketone). Such reaction products are more thermally stable than soluble carbohydrates and may be readily transformable into fuel blends and other materials through conducting one or more downstream reforming reactions. In addition, the foregoing types of reaction products are good solvents in which a hydrothermal digestion may be performed, thereby promoting solubilization of soluble carbohydrates as their reaction products during hydrothermal digestion.

A particularly effective manner in which soluble carbohydrates may be formed and converted into more stable compounds is through conducting the hydrothermal digestion of cellulosic biomass in the presence of molecular hydrogen and a slurry catalyst capable of activating the molecular hydrogen (also referred to herein as a "hydrogen-activating catalyst"). That is, in such approaches (termed "in situ catalytic reduction reaction processes" herein), the hydrothermal digestion of cellulosic biomass and the catalytic reduction of soluble carbohydrates produced therefrom may take place in the same vessel. As used herein, the term "slurry catalyst" will refer to a catalyst comprising fluidly mobile catalyst particles that can be at least partially suspended in a fluid phase via gas flow, liquid flow, mechanical agitation, or any combination thereof. If the slurry catalyst is sufficiently well distributed in the cellulosic biomass, soluble carbohydrates formed during hydrothermal digestion may be intercepted and converted into more stable compounds before they have had an opportunity to significantly degrade, even under thermal conditions that otherwise promote their degradation. Without adequate catalyst distribution being realized, soluble carbohydrates produced by in situ catalytic reduction reaction processes may still degrade before they have had an opportunity to encounter a catalytic site and undergo a stabilizing reaction. In situ catalytic reduction reaction processes may also be particularly advantageous from an energy efficiency standpoint, since hydrothermal digestion of cellulosic biomass is an endothermic process, whereas catalytic reduction reactions are exothermic. Thus, the excess heat generated by the in situ catalytic reduction reaction(s) may be utilized to drive the hydrothermal digestion with little opportunity for heat transfer loss to occur, thereby lowering the amount of additional heat energy input needed to conduct the digestion.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, valving, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

In addition to the desired carbohydrates, other substances may be present within cellulosic biomass that can be especially problematic to deal with in an energy- and cost-efficient manner Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. This issue is particularly significant for in situ catalytic reduction reaction processes, where there is minimal opportunity to address the presence of catalyst poisons, at least without significantly increasing process complexity and cost. As mentioned above, lignin can also be particularly problematic to deal with if it is not removed prior to beginning digestion. During cellulosic biomass processing, the significant quantities of lignin present in cellulosic biomass may lead to fouling of processing equipment, potentially leading to costly system down time. The significant lignin quantities can also lead to realization of a relatively low conversion of the cellulosic biomass into useable substances per unit weight of feedstock.

As evidenced by the foregoing, the efficient conversion of cellulosic biomass into fuel blends and other materials is a complex problem that presents immense engineering challenges. The present disclosure addresses these challenges and provides related advantages as well.

SUMMARY OF THE INVENTION

The present disclosure generally relates to digestion of cellulosic biomass solids, and, more specifically, to systems and methods in which cellulosic biomass solids may be processed in a hydrothermal digestion unit having a length and/or a width that is greater than its height.

In some embodiments, the present disclosure provides methods comprising: providing a hydrothermal digestion unit having a length or a width that is greater than its height, the hydrothermal digestion unit containing a fluid phase digestion medium and a slurry catalyst capable of activating molecular hydrogen; introducing cellulosic biomass solids to the hydrothermal digestion unit; distributing the cellulosic biomass solids laterally within the hydrothermal digestion unit, the fluid phase digestion medium at least partially covering the cellulosic biomass solids after they have been distributed; after or while the cellulosic biomass solids are being distributed, supplying an upwardly directed flow of molecular hydrogen through the cellulosic biomass solids and the fluid phase digestion medium; and heating the cellulosic biomass solids in the presence of the slurry catalyst and the molecular hydrogen, thereby forming an alcoholic component derived from the cellulosic biomass solids.

In some embodiments, the present disclosure provides biomass conversion systems comprising: a hydrothermal digestion unit having a length or a width that is greater than its height; a biomass feed mechanism that is operatively connected to the hydrothermal digestion unit, the biomass feed mechanism being configured for addition of cellulosic biomass solids to the hydrothermal digestion unit while the hydrothermal digestion unit is in a pressurized state; a gas distribution system laterally disposed within the hydrothermal digestion unit along its lower surface; and a fluid conduit configured to establish lateral fluid circulation within the hydrothermal digestion unit.

In some embodiments, the present disclosure provides methods comprising: providing a first hydrothermal digestion unit having a length or a width that is greater than its height, the first hydrothermal digestion unit containing a fluid phase digestion medium and a slurry catalyst capable of activating molecular hydrogen; introducing cellulosic biomass solids to the first hydrothermal digestion unit; distributing the cellulosic biomass solids laterally within the first hydrothermal digestion unit, the fluid phase digestion medium at least partially covering the cellulosic biomass solids after they have been distributed; after or while the cellulosic biomass solids are being distributed, supplying an upwardly directed flow of molecular hydrogen through the cellulosic biomass solids and the fluid phase digestion medium in the first hydrothermal digestion unit; heating the cellulosic biomass solids in the presence of the slurry catalyst and the molecular hydrogen in the first hydrothermal digestion unit, thereby forming partially digested cellulosic biomass solids and an alcoholic component derived from the cellulosic biomass solids; transferring the partially digested cellulosic biomass solids, the fluid phase digestion medium, and the slurry catalyst to a second hydrothermal digestion unit, the second hydrothermal digestion unit being fluidly coupled to the first hydrothermal digestion unit; supplying an upwardly directed flow of molecular hydrogen through the partially digested cellulosic biomass solids and the fluid phase digestion medium in the second hydrothermal digestion unit; and heating the partially digested cellulosic biomass solids in the presence of the slurry catalyst and the molecular hydrogen in the second hydrothermal digestion unit, thereby further forming the alcoholic component.

In some embodiments, the present disclosure provides biomass conversion systems comprising: a first hydrothermal digestion unit and a second hydrothermal digestion unit, the first hydrothermal digestion unit and the second hydrothermal digestion unit being fluidly coupled to one another, and at least the first hydrothermal digestion unit having a length or a width that is greater than its height; a biomass feed mechanism operatively connected to the first hydrothermal digestion unit, the biomass feed mechanism being configured for addition of cellulosic biomass solids to the first hydrothermal digestion unit while the first hydrothermal digestion unit is in a pressurized state; a gas distribution system disposed within each hydrothermal digestion unit along its lower surface; and a fluid conduit configured to establish lateral fluid circulation within the first hydrothermal digestion unit.

The features and advantages of the present disclosure will be readily apparent to one having ordinary skill in the art upon a reading of the description of the embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
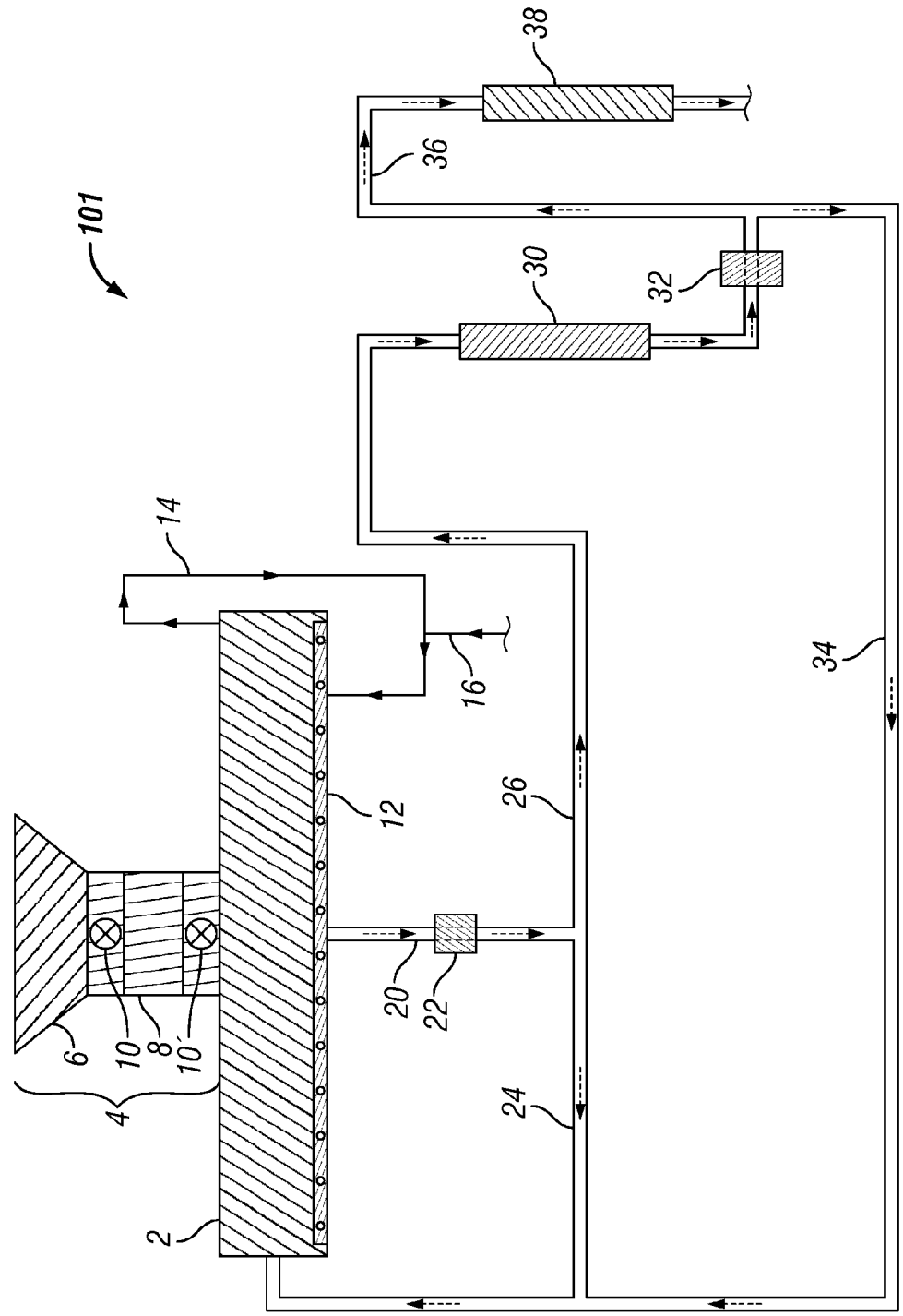
FIGS. 1-4 show schematics of illustrative biomass conversion systems containing a horizontally configured hydrothermal digestion unit.

The present disclosure generally relates to digestion of cellulosic biomass solids, and, more specifically, to systems and methods in which cellulosic biomass solids may be processed in a hydrothermal digestion unit having a length and/or a width that is greater than its height.

In the embodiments described herein, the digestion rate of cellulosic biomass solids may be accelerated in the presence of a fluid phase digestion medium comprising a digestion solvent. In some instances, the fluid phase digestion medium may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures, as discussed above. As further discussed above, one approach for addressing the degradation of soluble carbohydrates during hydrothermal digestion is to conduct an in situ catalytic reduction reaction process so as to convert the soluble carbohydrates into more stable compounds as soon as possible after their formation.

Although digesting cellulosic biomass solids by an in situ catalytic reduction reaction process may be particularly advantageous for at least the reasons noted above, successfully executing such a coupled approach may be problematic in other aspects. One significant issue that may be encountered is that of adequate catalyst distribution within the digesting cellulosic biomass solids, since insufficient catalyst distribution can result in poor stabilization of soluble carbohydrates. The present inventors discovered that, in certain instances, a slurry catalyst may be effectively distributed from the bottom of a charge of cellulosic biomass solids to the top by using upwardly directed fluid flow to fluidize and upwardly convey slurry catalyst particulates into the interstitial spaces within the charge. Suitable techniques for using fluid flow to distribute a slurry catalyst within cellulosic biomass solids in such a manner are described in commonly owned US20140005445 and US20140005444, and incorporated herein by reference in its entirety. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Such approaches may also address the problem of cellulosic biomass fines, since they may be co-flowed with the motive fluid.

As noted above, when the vertical height of a charge of cellulosic biomass solids increases, compaction of the cellulosic biomass solids in the lower portions of the charge may become problematic. More specifically, as the height of a vertical column of cellulosic biomass solids increases, the pressure on the lower portions of the column also increases. In partially digested, structurally compromised cellulosic biomass solids, the weight of the upper cellulosic biomass solids can collapse the lower cellulosic biomass solids. If biomass compaction cannot be sufficiently reduced by upwardly directed fluid flow, it may be difficult to attain an effective distribution of the slurry catalyst in the cellulosic biomass solids. Moreover, as the vertical height of a charge of cellulosic biomass solids increases, it may become more difficult to sufficiently fluidize the slurry catalyst particulates such that they can be fluidly conveyed to the upper reaches of the charge.

In addition to the aforementioned issues associated with slurry catalyst distribution and biomass compaction that may occur as the vertical height of a charge of cellulosic biomass solids becomes large, effective distribution of molecular hydrogen may also become problematic, as described in commonly owned U.S. Patent Applications 61/740,006 and 61/740,039, each filed on Dec. 20, 2012 and incorporated herein by reference in its entirety. As with a poorly distributed slurry catalyst, inadequate distribution of molecular hydrogen in cellulosic biomass solids can likewise result in poor stabilization of soluble carbohydrates during in situ catalytic reduction reaction processes. Without being bound by any theory or mechanism, it is believed that a poor distribution of molecular hydrogen within cellulosic biomass solids may be realized due to a coalescence of introduced molecular hydrogen into large bubbles that are unable to penetrate into the interstitial spaces within a charge of digesting cellulosic biomass solids. As the vertical height of a charge of cellulosic biomass solids in contact with a continuous liquid phase increases, the propensity toward hydrogen bubble coalescence may be increased.

The present inventors recognized that the problems of biomass compaction, slurry catalyst distribution, and hydrogen bubble coalescence might be simultaneously addressed by altering the configuration of a hydrothermal digestion unit being used to digest cellulosic biomass solids from a substantially vertical configuration into a horizontal configuration in which the length and/or width of the hydrothermal digestion unit is greater than its height. As used herein, the term "horizontal digestion unit" will be used to refer to a hydrothermal digestion unit having a length and/or width that is greater than its height. Likewise, the term "vertical digestion unit" will be used herein to refer to a hydrothermal digestion unit that has a height that is greater than its length and/or width. By digesting a charge of cellulosic biomass solids in a horizontal digestion unit, the thickness of the charge may be more limited than in a vertical configuration having an equivalent working volume for processing cellulosic biomass solids. Reducing the thickness of the charge in such a manner may reduce the aforementioned compaction issues, since there are fewer cellulosic biomass solids exerting pressure on the lower reaches of the charge and the downward force is spread out over a larger area than in an equivalent vertical configuration. Moreover, the downward load may also be more effectively transferred to the lower wall of the hydrothermal digestion unit in such configurations. In addition, a reduced thickness of the charge of cellulosic biomass solids may facilitate expansion of the cellulosic biomass solids using upwardly directed fluid flow. Finally, a reduced thickness of the charge of cellulosic biomass solids may promote better distribution of both the slurry catalyst and molecular hydrogen therein, since there is a decreased vertical height through which the slurry catalyst and molecular hydrogen need to be conveyed.

In addition to the above, further advantages may also be realized by utilizing a horizontal digestion unit. For a fixed vertical height, a horizontal digestion unit may be configured to provide a longer digestion medium contact time than can be realized for a vertical digestion unit of comparable volume. Aviation safety restrictions may place vertical height limitations on refinery components that can limit their throughput in commercial operations. By reconfiguring a hydrothermal digestion unit from a vertical into a horizontal configuration that is not particularly limited in length by aviation restrictions, the path length of the cellulosic biomass solids through the horizontal digestion unit may be increased. For example, by passing the cellulosic biomass solids laterally within the horizontal digestion unit from one end to another, the path length and contact time with a fluid phase digestion medium therein may be increased compared to a vertical digestion unit of equivalent height. While a horizontal digestion unit may have an increased operational "footprint" compared to a vertical digestion unit, this limitation may be mitigated by its potential for increased throughput.

When utilizing a horizontal hydrothermal digestion unit, one difficulty that may be encountered is how to effectively fill the hydrothermal digestion unit with cellulosic biomass solids. In a vertical digestion unit, cellulosic biomass solids may pile upon one another under the influence of gravity and fill the available digestion unit volume. Likewise, in an inclined digestion unit, the influence of gravity may be used to promote effective filling of the digestion unit volume with cellulosic biomass solids, as described in commonly owned U.S. Patent Application 61/817,990 entitled "Methods and Systems Employing an Inclined Digestion Unit for Hydrothermal Digestion of Cellulosic Biomass Solids," filed concurrently herewith and incorporated herein by reference in its entirety. In a horizontal digestion unit, in contrast, the influence of gravity may only promote filling of the digestion unit volume to a limited degree below or near the location of cellulosic biomass solids introduction. Filling only a portion of the hydrothermal digestion unit can reduce its throughput capabilities and reduce the effective contact time of the cellulosic biomass solids with the digestion medium. As described herein, active measures may be taken to promote lateral distribution of the cellulosic biomass solids within the hydrothermal digestion unit in order to address the foregoing issues. Moreover, the native properties of cellulosic biomass solids and their interaction with a fluid phase digestion medium may also be used to promote their lateral distribution within a hydrothermal digestion unit.

In addition to the foregoing advantages, a horizontal digestion unit may remain compatible with techniques used for addressing the formation of heterogeneous liquid phases during hydrothermal digestion of cellulosic biomass solids. While digesting cellulosic biomass solids by an in situ catalytic reduction reaction process in the presence of a slurry catalyst and an aqueous phase digestion solvent, where the cellulosic biomass solids were supplied on an ongoing basis, the present inventors discovered that lignin from the cellulosic biomass solids eventually separated as a phenolics liquid phase that was neither fully dissolved nor fully precipitated, but instead formed as a discrete liquid phase that was highly viscous and hydrophobic. The slurry catalyst was well wetted by the phenolics liquid phase and accumulated therein over time, thereby making the slurry catalyst less readily distributable in the cellulosic biomass solids (e.g., by using upwardly directed fluid flow). In many instances, the phenolics liquid phase was located below the aqueous phase, which also contained an alcoholic component derived from the cellulosic biomass solids via a catalytic reduction reaction of soluble carbohydrates. Depending on the ratio of water and organic solvent in the digestion solvent, rates of fluid flow, catalyst identity, reaction times and temperatures, and the like, a light organics phase was also sometimes observed, typically located above the aqueous phase, where the components of the light organics phase were also derived, at least in part, from the cellulosic materials in the biomass. Components present in the light organics phase included, for example, the alcoholic component derived from the cellulosic biomass solids, including $C_4$ or greater alcohols, and self-condensation products, such as those obtained by the acid-catalyzed Aldol reaction. The alcoholic component in the resulting two- or three-phase liquid mixture may be processed as described in more detail in commonly owned U.S. Patent Applications 61/720,689 and 61/720,747, each filed on Oct. 31, 2012 and incorporated herein by reference in its entirety.

Techniques for mitigating the accumulation of a slurry catalyst in a phenolics liquid phase are described in more detail in commonly owned U.S. Patent Application 61/720,757, filed on Oct. 31, 2012 and incorporated herein by reference in its entirety. As described therein, the accumulated slurry catalyst within the phenolics liquid phase may be conveyed from a lower portion of the hydrothermal digestion unit to a location above the cellulosic biomass solids and released, such that the slurry catalyst then contacts the cellulosic biomass solids. By conveying the accumulated slurry catalyst in such a manner, the slurry catalyst may become redistributed in the cellulosic biomass solids as the phenolics liquid phase percolates downward through the cellulosic biomass solids, rather than from becoming distributed via upwardly directed fluid flow. As described herein, such techniques may be practiced in a related manner when hydrothermal digestion is performed using a horizontal digestion unit.

Unless otherwise specified, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product comprising a monohydric alcohol, a glycol, a triol, or any combination thereof, at least some of which may also contain a carbonyl functionality. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof.

As used herein, the term "phenolics liquid phase" will refer to a fluid phase comprising liquefied lignin. In some embodiments, the phenolics liquid phase may be more dense than water, but it may also be less dense than water depending on lignin concentrations and the presence of other components, for example.

As used herein, the term "alcoholic component" will refer to a monohydric alcohol, glycol, triol, or any combination thereof that is formed from a catalytic reduction reaction of soluble carbohydrates derived from cellulosic biomass solids.

As used herein, the term "light organics phase" will refer to a fluid phase that is typically less dense than water and comprises an organic compound. The organic compound may include at least a portion of the alcoholic component formed via catalytic reduction of soluble carbohydrates, which may include $C_4$ or greater alcohols and self-condensation products thereof.

As used herein, the term "horizontal" and other grammatical forms thereof will refer to the condition of a surface being oriented at an angle of about 5 degrees or less relative to the earth's surface.

As used herein, the term "vertical" and other grammatical forms thereof will refer to the condition of a surface being oriented at an angle ranging between about 85 degrees and about 90 degrees relative to the earth's surface.

As used herein, the terms "lateral" and "laterally" will refer to a lengthwise disposition within or about an elongated structure.

As used herein, the term "upwardly directed" will refer to a direction of fluid flow from a surface that is non-parallel to the surface.

In some embodiments, methods described herein can comprise: providing a hydrothermal digestion unit having a length or a width that is greater than its height, the hydrothermal digestion unit containing a fluid phase digestion medium and a slurry catalyst capable of activating molecular hydrogen; introducing cellulosic biomass solids to the hydrothermal digestion unit; distributing the cellulosic biomass solids laterally within the hydrothermal digestion unit, the fluid phase digestion medium at least partially covering the cellulosic biomass solids after they have been distributed; after or while the cellulosic biomass solids are being distributed, supplying an upwardly directed flow of molecular hydrogen through the cellulosic biomass solids and the fluid phase digestion medium; and heating the cellulosic biomass solids in the presence of the slurry catalyst and the molecular hydrogen, thereby forming an alcoholic component derived from the cellulosic biomass solids.

As described above, in some embodiments, the upwardly directed flow of molecular hydrogen may at least partially distribute the slurry catalyst in the cellulosic biomass solids. As used herein, the terms "at least partially distribute" and "distribute at least a portion of" will be used synonymously with one another. In some or other embodiments, a fluid phase containing the slurry catalyst may be conveyed from a first location in the hydrothermal digestion unit to a second location in the hydrothermal digestion unit in order to affect distribution of the slurry catalyst. For example, in some embodiments, a fluid phase digestion medium containing the slurry catalyst or a phenolics liquid phase containing the slurry catalyst may be conveyed from a lower portion of the hydrothermal digestion unit to a location above at least a portion of the cellulosic biomass and released. Upon being released, the slurry catalyst may percolate downward through the cellulosic biomass solids, thereby affecting distribution thereof. Before being released, the slurry catalyst in the fluid phase may be conveyed laterally within the hydrothermal digestion unit, such that the slurry catalyst is laterally distributed in the cellulosic biomass solids once released.

In some embodiments, the hydrothermal digestion unit may contain the fluid phase digestion medium and the slurry catalyst when the cellulosic biomass solids are introduced thereto. In other embodiments, the cellulosic biomass solids may first be added to the hydrothermal digestion, with introduction of the fluid phase digestion medium and the slurry catalyst taking place thereafter. In still other embodiments, introduction of the fluid phase digestion medium and the slurry catalyst may take place concurrently with introduction of the cellulosic biomass solids. For example, in some embodiments, a recirculation flow of the fluid phase digestion medium and the slurry catalyst may be introduced to the hydrothermal digestion unit while the cellulosic biomass solids are being added. As discussed hereinbelow, the recirculation flow may promote the lateral distribution of the cellulosic biomass solids in the hydrothermal digestion unit.

Various techniques may be used for laterally distributing the cellulosic biomass solids in the hydrothermal digestion unit. In some embodiments, the native properties of the cellulosic biomass solids themselves may be used to promote their lateral distribution in the hydrothermal digestion unit. One feature that cellulosic biomass solids may possess is that they may float on a fluid phase digestion medium, until they are sufficiently infiltrated with the fluid phase digestion medium and then sink. In a vertically configured hydrothermal digestion unit, floating cellulosic biomass solids may be problematic, since it can be difficult to introduce additional material through the floating cellulosic biomass. However, in a horizontal digestion unit, floatation of the cellulosic biomass solids may desirably promote lateral distribution of the cellulosic biomass solids therein. More specifically, in some embodiments, the cellulosic biomass solids may be distributed laterally within the hydrothermal digestion unit by floating the cellulosic biomass solids on the fluid phase digestion medium, such that they laterally disperse away from a location of their introduction. As the cellulosic biomass solids become laterally distributed through the hydrothermal digestion unit, they may become infiltrated with the fluid phase digestion medium and eventually sink. Once the cellulosic biomass solids have sunk, additional floating cellulosic biomass solids may become laterally distributed in the hydrothermal digestion unit. Moreover, once the cellulosic biomass solids have sunk in the fluid phase digestion medium, they may be better suited to undergo hydrothemal digestion through increased digestion medium contact.

In some embodiments, fluid motion of the fluid phase digestion medium may be used to promote lateral distribution of the cellulosic biomass solids in the hydrothermal digestion unit. Fluid motion may be used solely to laterally distribute the cellulosic biomass solids, or fluid motion may be used in combination with other biomass distribution techniques described herein. For example, in some embodiments, fluid motion may be used to affect lateral distribution of floating, submerged, or partially submerged cellulosic biomass solids in the hydrothermal digestion unit. In such embodiments, fluid motion may fluidize the cellulosic biomass solids and affect their conveyance from one end of the hydrothermal digestion unit to the other. During their transit through the hydrothermal digestion unit, the cellulosic biomass solids may undergo hydrothermal digestion to produce soluble carbohydrates, followed by stabilization of the soluble carbohydrates through a catalytic reduction reaction. As discussed above, the lateral transit of the cellulosic biomass solids through the hydrothermal digestion unit may result in increased contact times with the fluid phase digestion medium relative to comparable vertical digestion units.

In more specific embodiments, the cellulosic biomass solids may be distributed laterally within the hydrothermal digestion unit by circulating the fluid phase digestion medium and the slurry catalyst laterally therethrough. As used herein, the terms "circulate," "circulation" and other variants thereof will be used to refer to the removal of a substance from the hydrothermal digestion unit, followed by the subsequent return of the substance to the hydrothermal digestion unit one or more times. As described hereinafter, providing the upwardly directed flow of molecular hydrogen may also be performed by circulating the molecular hydrogen through the hydrothermal digestion unit. In addition to promoting lateral distribution of the cellulosic biomass solids, lateral circulation of the fluid phase digestion medium may allow other advantages to be realized as well. For example, by circulating the fluid phase digestion medium laterally through the hydrothermal digestion unit, thermal variations within the hydrothermal digestion unit may be lessened. Moreover, by circulating the slurry catalyst within the fluid phase digestion medium, the slurry catalyst may be distributed both horizontally and vertically within the hydrothermal digestion unit. Specifically, the slurry catalyst may be distributed vertically by the upwardly directed flow of molecular hydrogen and horizontally by the circulating fluid phase digestion medium. In some embodiments, the fluid phase digestion medium may circulate through the hydrothermal digestion unit from one end to the other in accomplishing the foregoing. Moreover, the fluid phase digestion medium may circulate to another fluidly coupled hydrothermal digestion unit to affect the conveyance of cellulosic biomass solids thereto, as discussed hereinbelow.

Figure 2:
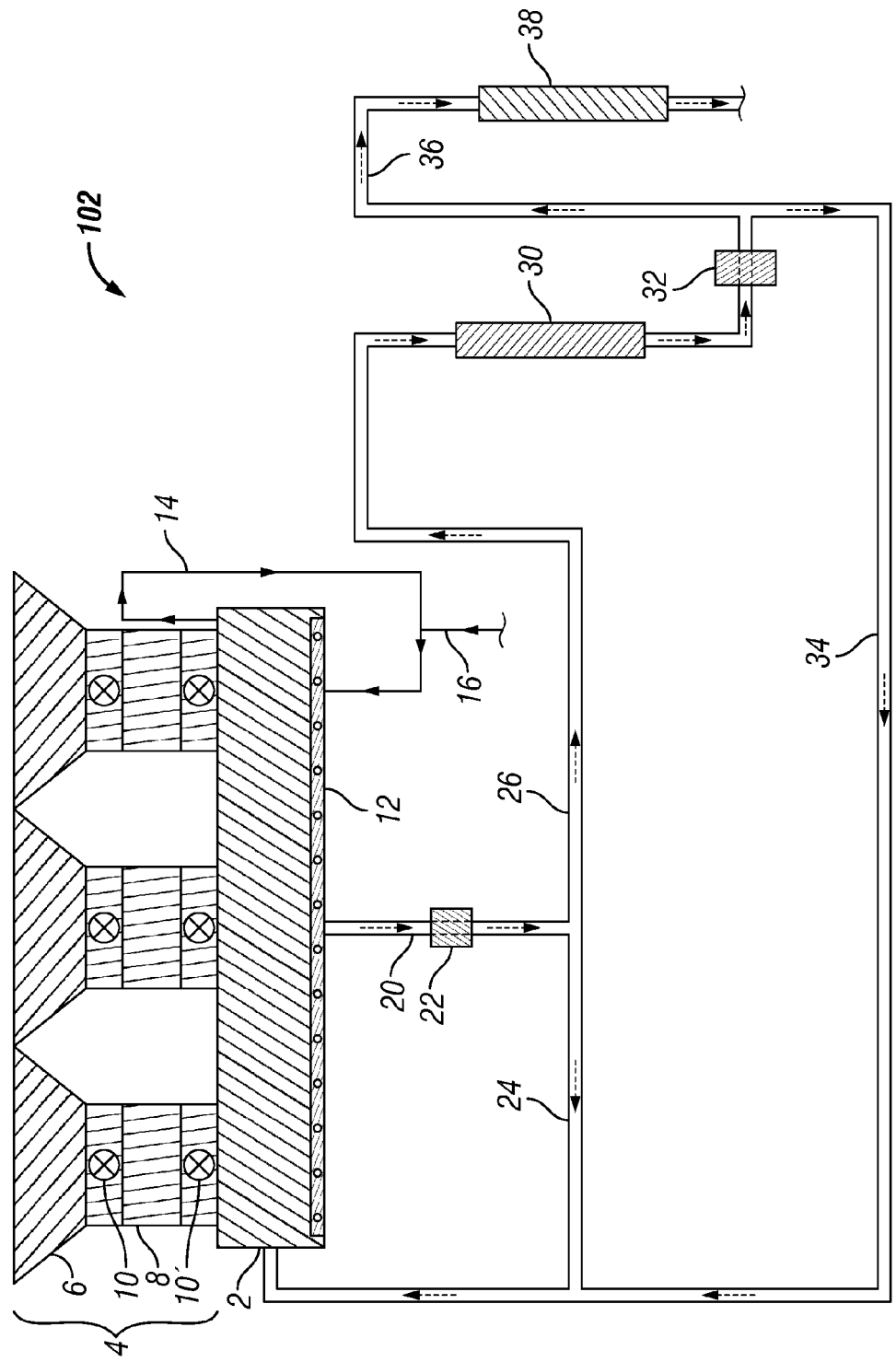

Lateral distribution of the cellulosic biomass solids within the hydrothermal digestion unit may be accomplished by other techniques as well. In some embodiments, cellulosic biomass solids may be introduced to the hydrothermal digestion unit at a plurality of locations disposed laterally about an upper surface of the hydrothermal digestion unit, as generally depicted in FIG. 2. By introducing cellulosic biomass solids to the hydrothermal digestion unit at multiple locations, there may be a reduced need to laterally distribute the cellulosic biomass solids once in the hydrothermal digestion unit, since they are "pre-distributed" prior to their introduction thereto. Suitable mechanisms for introducing cellulosic biomass solids to a pressurized hydrothermal digestion unit are discussed hereinbelow. It is to be noted that lateral circulation of the fluid phase digestion medium may still be used in combination with this lateral distribution technique, even if such fluid motion is not directly used to promote lateral distribution of the cellulosic biomass solids in the hydrothermal digestion unit.

Figure 4:
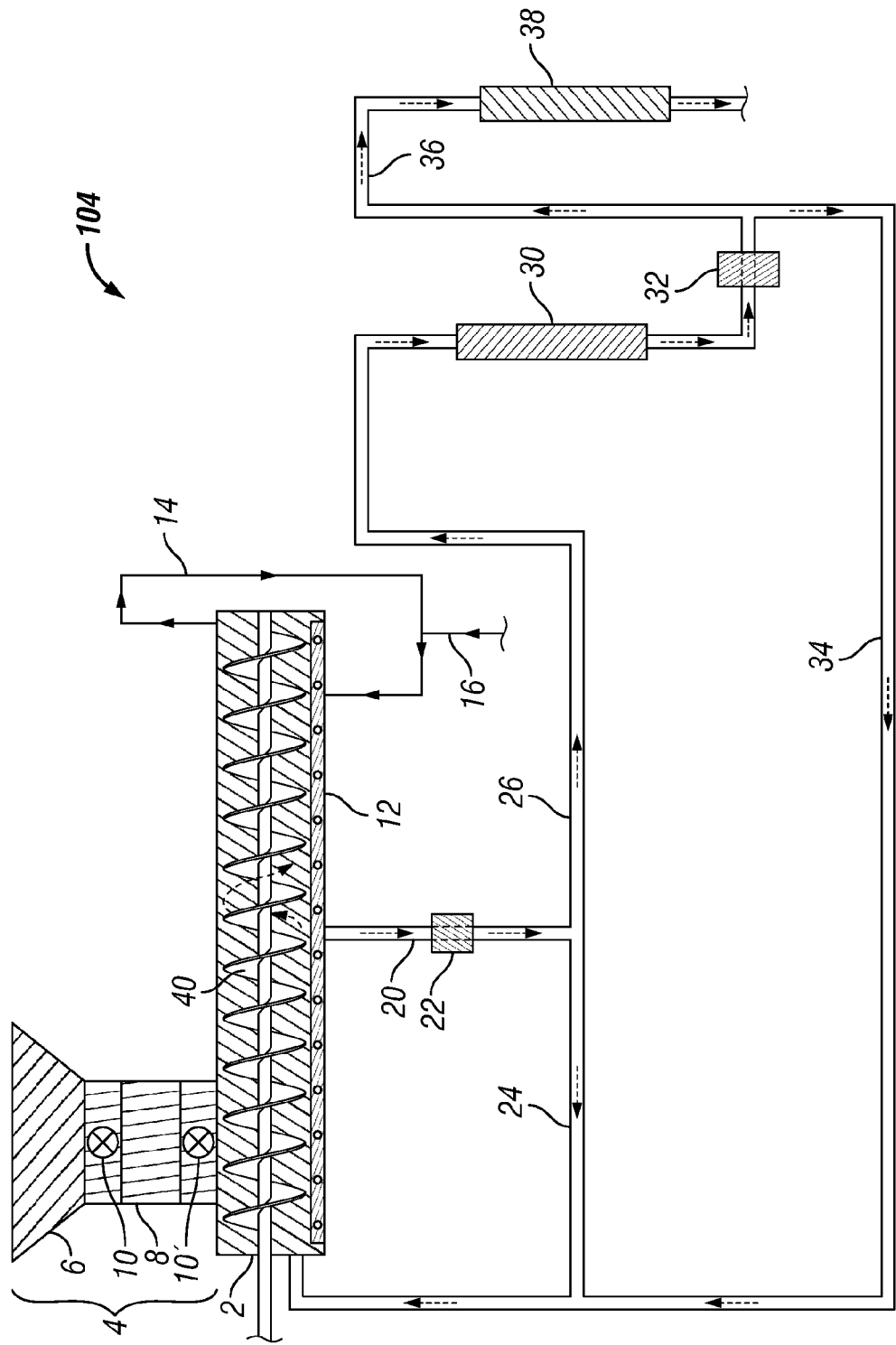

In still other embodiments, mechanical means for laterally distributing the cellulosic biomass solids within the hydrothermal digestion unit may be employed. That is, in some embodiments, the cellulosic biomass solids may be laterally distributed within the hydrothermal digestion unit through use of a solids transport mechanism located therein, as depicted in FIG. 4. In some embodiments, a suitable solids transport mechanism may comprise a screw impeller, particularly a vanishing screw impeller. Other mechanical means for laterally conveying cellulosic biomass solids within a pressurized hydrothermal digestion unit may be envisioned by one having ordinary skill in the art. It is to be noted that lateral circulation of the fluid phase digestion medium may still be used in combination with this lateral distribution technique, even if such fluid motion is not directly used to promote lateral distribution of the cellulosic biomass solids in the hydrothermal digestion unit.

Lateral fluid circulation in the hydrothermal digestion unit may be established by removing the fluid phase digestion medium or another fluid phase from the hydrothermal digestion unit and subsequently returning it thereto. For example, in some embodiments, methods described herein may further comprise removing at least a portion of the fluid phase digestion medium and the slurry catalyst from the hydrothermal digestion unit, after the alcoholic component has been formed or while the alcoholic component is being formed. In some embodiments, the methods may further comprise returning at least a portion of the fluid phase digestion medium and the slurry catalyst to the hydrothermal digestion unit, and circulating at least a portion of the fluid phase digestion medium and the slurry catalyst laterally through the hydrothermal digestion unit. In alternative embodiments, the slurry catalyst may be separated from the fluid phase digestion unit being returned to the hydrothermal digestion unit, or the fluid phase digestion medium may be processed in some manner to promote return of the slurry catalyst. In other alternative embodiments, the slurry catalyst may be regenerated before being returned to the hydrothermal digestion unit. In still other alternative embodiments, a fluid phase other than the fluid phase digestion medium may be circulated through the hydrothermal digestion unit. For example, in some embodiments, a phenolics liquid phase containing the slurry catalyst may be circulated laterally through the hydrothermal digestion unit, either alone or in combination with the fluid phase digestion medium.

The fluid phase digestion medium or other fluid phase being circulated through the hydrothermal digestion unit may flow with either countercurrent or co-current flow relative to the direction in which cellulosic biomass solids are being laterally distributed in the hydrothermal digestion unit. In some embodiments, the fluid phase digestion medium and the slurry catalyst may be circulated laterally through the hydrothermal digestion unit in the same direction in which the cellulosic biomass solids are being distributed in the hydrothermal digestion unit. Such co-current flow circulation of the fluid phase digestion medium and slurry catalyst desirably provides the slurry catalyst to the cellulosic biomass solids at an early point in their hydrothermal digestion. However, in alternative embodiments, the fluid phase digestion medium and the slurry catalyst may be circulated laterally in the hydrothermal digestion unit with countercurrent flow. Countercurrent flow may be used, for example, to slow the lateral progression of cellulosic biomass solids through the hydrothermal digestion unit, if desired.

In some embodiments, the hydrothermal digestion of cellulosic biomass solids may take place in multiple hydrothermal digestion units that are fluidly coupled to one another. More specifically, in some embodiments, the cellulosic biomass solids may be partially digested in a first hydrothermal digestion unit, and hydrothermal digestion of the partially digested cellulosic biomass solids may then be continued or completed in a second or subsequent hydrothermal digestion unit. In such embodiments, the hydrothermal digestion conditions in the fluidly coupled hydrothermal digestion units may be the same or different (e.g., different temperatures, solvents, flow rates, and the like).

In some embodiments, methods described herein may comprise: providing a first hydrothermal digestion unit having a length or a width that is greater than its height, the first hydrothermal digestion unit containing a fluid phase digestion medium and a slurry catalyst capable of activating molecular hydrogen; introducing cellulosic biomass solids to the first hydrothermal digestion unit; distributing the cellulosic biomass solids laterally within the first hydrothermal digestion unit, the fluid phase digestion medium at least partially covering the cellulosic biomass solids after they have been distributed; after or while the cellulosic biomass solids are being distributed, supplying an upwardly directed flow of molecular hydrogen through the cellulosic biomass solids and the fluid phase digestion medium in the first hydrothermal digestion unit; heating the cellulosic biomass solids in the presence of the slurry catalyst and the molecular hydrogen in the first hydrothermal digestion unit, thereby forming partially digested cellulosic biomass solids and an alcoholic component derived from the cellulosic biomass solids; transferring the partially digested cellulosic biomass solids, the fluid phase digestion medium, and the slurry catalyst to a second hydrothermal digestion unit, the second hydrothermal digestion unit being fluidly coupled to the first hydrothermal digestion unit; supplying an upwardly directed flow of molecular hydrogen through the partially digested cellulosic biomass solids and the fluid phase digestion medium in the second hydrothermal digestion unit; and heating the partially digested cellulosic biomass solids in the presence of the slurry catalyst and the molecular hydrogen in the second hydrothermal digestion unit, thereby further forming the alcoholic component.

When two or more fluidly coupled hydrothermal digestion units are used in the embodiments described herein, only the first hydrothermal digestion unit needs to have a length or a width that is greater than its height (i.e., be oriented in a horizontal configuration). In some embodiments described herein, the second hydrothermal digestion unit may have a height that is greater than its length or its width. That is, in such embodiments, the second hydrothermal digestion unit may be oriented in a vertical configuration. In other embodiments described herein, the second hydrothermal digestion unit may have a length or width that is greater than its height. That is, in such embodiments, the second hydrothermal digestion unit may be oriented in a horizontal configuration.

Various configurations for the fluid coupling between the first hydrothermal digestion unit and the second hydrothermal digestion unit are possible. In some embodiments, the bottom of the first hydrothermal digestion unit may be fluidly coupled to the top of the second hydrothermal digestion unit. That is, in such embodiments, the first hydrothermal digestion unit and the second hydrothermal digestion unit may be stacked upon one another. In such embodiments, the second hydrothermal digestion unit may be oriented in a vertical or a horizontal configuration, and one or more second hydrothermal digestion units may be present. Further description of such configurations are discussed in more detail hereinbelow with reference to the drawings.

In other various embodiments, the first hydrothermal digestion unit may be fluidly coupled to the second hydrothermal digestion unit via the end or via the side of the first hydrothermal digestion unit. That is, in such embodiments, the first hydrothermal digestion unit and the second hydrothermal digestion unit may be disposed side-by-side or end-to-end relative to one another. In more specific embodiments, the first hydrothermal digestion unit and the second hydrothermal digestion unit may be fluidly coupled end-to-end. In other embodiments, however, the first hydrothermal digestion unit and the second hydrothermal digestion unit may be configured such that the end or the side of the first hydrothermal digestion unit is fluidly coupled to the top of the second hydrothermal digestion unit. Further description of such configurations are discussed in more detail hereinbelow with reference to the drawings.

In some embodiments, the upwardly directed flow of molecular hydrogen through the cellulosic biomass solids and the fluid phase digestion medium in the hydrothermal digestion unit(s) may be supplied from a gas distribution system that is disposed laterally within the hydrothermal digestion unit(s). More specifically, the gas distribution system may be laterally disposed on or near the bottom surface of the hydrothermal digestion unit(s) such that the gas distribution system can provide molecular hydrogen flow to cellulosic biomass solids residing above. In various embodiments, the gas distribution system may be disposed substantially parallel to the bottom surface of the hydrothermal digestion unit(s). As described above, molecular hydrogen so introduced may mediate stabilization of soluble carbohydrates both by serving as a reactant for a catalytic reduction reaction and promoting distribution of a slurry catalyst in the cellulosic biomass solids. Suitable gas distribution systems may include slotted distributors, manifolds, empty piping with an array of holes disposed thereon, sintered metal elements, collections of nozzles at a spacing effective to disperse a gas phase, other gas distribution manifolds, combinations thereof and the like.

In some embodiments, molecular hydrogen being supplied to the gas distribution system may be supplied from a molecular hydrogen source external to the hydrothermal digestion unit. In some or other embodiments, the molecular hydrogen being supplied to the gas distribution system may be recycled from one section of the hydrothermal digestion unit to another. More specifically, in some embodiments, the methods described herein may further comprise recirculating at least a portion of the molecular hydrogen in the hydrothermal digestion unit(s) from a headspace of the hydrothermal digestion unit(s) to a source of the upwardly directed flow of molecular hydrogen therein. For example, the source of the upwardly directed fluid flow may comprise a gas distribution system contained in the hydrothermal digestion unit(s). When multiple hydrothermal digestion units are present, molecular hydrogen may be recirculated from a first hydrothermal digestion unit to a second hydrothermal digestion unit, or it may be recirculated within the same hydrothermal digestion unit. In embodiments where the first hydrothermal digestion unit and the second hydrothermal digestion unit are stacked upon one another, molecular hydrogen may be recirculated from a headspace of the first hydrothermal digestion unit to the bottom of the second hydrothermal digestion unit. Thereafter, the molecular hydrogen may be transferred from a headspace of the second hydrothermal digestion unit to the bottom of the first hydrothermal digestion unit to establish a continuous flow loop of molecular hydrogen circulation. By transferring and recycling molecular hydrogen in the foregoing manner, more efficient use of the molecular hydrogen can be realized than without recycling taking place. For example, transferring molecular hydrogen in the foregoing manner may allow molecular hydrogen that has collected in a headspace above the cellulosic biomass solids and is no longer promoting stabilization of soluble carbohydrates therein to be redistributed to other cellulosic biomass solids for continued promotion of soluble carbohydrate stabilization. Although molecular hydrogen may be transferred between hydrothermal digestion units in the foregoing manner, it is to be recognized that in other embodiments, each hydrothermal digestion unit may be supplied with separate feeds of molecular hydrogen, if desired. In such embodiments, the excess molecular hydrogen exiting each hydrothermal digestion unit may be combined and then recirculated to one or more hydrothermal digestion units. Separate molecular hydrogen feeds may be desirable if hydrothermal digestion is conducted at different temperatures in each hydrothermal digestion unit, in which case, the rate of molecular hydrogen consumption may differ in each hydrothermal digestion unit.

In some embodiments, a feed for the gas distribution system may enter the hydrothermal digestion unit at a level above that of the fluid phase digestion medium contained therein. Advantages of the feed entering the hydrothermal digestion unit in such a manner may include limiting the possibility of plugging the feed with the fluid phase digestion medium and the cellulosic biomass solids. If the gas distribution system fills with a fluid phase or a mixed fluid phase and solid phase, it will no longer be possible to distribute a gas therethrough in the absence of gas phase recompression. However, if a feed line to the gas distribution mechanism rises to an elevation higher than the maximum liquid elevation within the inclined tubular element before descending into the gas distribution mechanism, then it is not possible for a fluid phase to flow into the gas distribution system when gas flow is stopped, thereby reducing the likelihood of plugging and lowering the needed gas flow rates.

Before discussing other various aspects of the above methods, illustrative biomass conversion systems suitable for practicing the methods set forth herein will now be described in greater detail. As described hereinafter, the biomass conversion systems may comprise one or more hydrothermal digestion units having a length or a width that is greater than its height.

In some embodiments, biomass conversion systems described herein may comprise: a hydrothermal digestion unit having a length or a width that is greater than its height; a biomass feed mechanism that is operatively connected to the hydrothermal digestion unit, the biomass feed mechanism being configured for addition of cellulosic biomass solids to the hydrothermal digestion unit while the hydrothermal digestion unit is in a pressurized state; a gas distribution system laterally disposed within the hydrothermal digestion unit along its lower surface; and a fluid conduit configured to establish lateral fluid circulation within the hydrothermal digestion unit. Further description of the location of the gas distribution system within the hydrothermal digestion unit is set forth in more detail above.

In other embodiments, biomass conversion systems described herein may comprise: a first hydrothermal digestion unit and a second hydrothermal digestion unit, the first hydrothermal digestion unit and the second hydrothermal digestion unit being fluidly coupled to one another, and at least the first hydrothermal digestion unit having a length or a width that is greater than its height; a biomass feed mechanism operatively connected to the first hydrothermal digestion unit, the biomass feed mechanism being configured for addition of cellulosic biomass solids to the first hydrothermal digestion unit while the first hydrothermal digestion unit is in a pressurized state; a gas distribution system disposed within each hydrothermal digestion unit along its lower surface; and a fluid conduit configured to establish lateral fluid circulation within the first hydrothermal digestion unit. Further description of the location of the gas distribution system within each hydrothermal digestion unit is set forth in more detail above.

In embodiments where both a first hydrothermal digestion unit and a second hydrothermal digestion unit are present, the second hydrothermal digestion unit may be oriented in a vertical configuration or a horizontal configuration, as discussed above. More specifically, in some embodiments, the second hydrothermal digestion unit may have a height that is greater than its length or its width. In other embodiments, the second hydrothermal digestion unit may have a length or a width that is greater than its height. In various embodiments, the first hydrothermal digestion unit may be fluidly coupled to the second hydrothermal digestion unit bottom-to-top, end-to-end, or side-to-side, as discussed in more detail above. Moreover, in various embodiments, the first hydrothermal digestion unit may be fluidly coupled to the second hydrothermal digestion unit at a single location or at two or more locations.

In some embodiments, a solids transport mechanism may be present within the hydrothermal digestion unit. For example, in some embodiments, the solids transport mechanism may comprise a screw impeller.

In some embodiments, the biomass conversion systems may further comprise a gas recycle line configured to establish fluid communication between a headspace of a hydrothermal digestion unit and a gas distribution system. In embodiments where a single hydrothermal digestion unit is present, the gas recycle line may be configured to establish fluid communication between a headspace of the hydrothermal digestion unit and the gas distribution system therein. In embodiments where two or more hydrothermal digestion units are present and fluidly coupled to one another, the gas recycle line may be configured to establish fluid communication between a headspace of either hydrothermal digestion unit with the same hydrothermal digestion unit and/or a different hydrothermal digestion unit. More specifically, in some embodiments, the gas recycle line may be configured to establish fluid communication between a headspace of the first hydrothermal digestion unit and the gas distribution line in the first hydrothermal digestion unit or the second hydrothermal digestion unit. In some or other embodiments, the gas recycle line may be configured to establish fluid communication between a headspace of the second hydrothermal digestion unit and the gas distribution system in the first hydrothermal digestion unit or the second hydrothermal digestion unit.

It is to be understood that an uncirculated gas may be introduced to the gas distribution system in combination with or as an alternative to a recirculated gas. For example, a gas supply line may be fluidly connected to the each gas distribution system. The gas supply line may be used for initial pressurization and/or to maintain the gas pressure at a desired level during hydrothermal digestion.

As discussed above, the biomass conversion systems described herein may contain a fluid conduit configured to establish lateral fluid circulation within the hydrothermal digestion unit. When one hydrothermal digestion unit is present, the fluid conduit may be configured as a fluid circulation loop that conveys a fluid from one end of the hydrothermal digestion unit to another. As discussed above, lateral fluid circulation produced in such configurations may promote the lateral distribution of cellulosic biomass solids in the hydrothermal digestion unit. When more than one hydrothermal digestion unit is present, the fluid conduit may again be configured as a fluid circulation loop, this time fluidly connecting two or more hydrothermal digestion units. In some embodiments, the fluid conduit may be configured as a fluid circulation loop to convey a fluid from the second hydrothermal digestion unit to the first hydrothermal digestion unit, with fluid circulation in the fluid circulation loop taking place along the fluid connection between the first hydrothermal digestion unit and the second hydrothermal digestion unit. In some embodiments, the fluid circulation within the fluid connection between the first hydrothermal digestion unit and the second hydrothermal digestion unit may be sufficient to carry cellulosic biomass solids and slurry catalyst from the first hydrothermal digestion unit to the second hydrothermal digestion unit. As described above, the lateral fluid circulation in the hydrothermal digestion unit established by the fluid conduit may be in the same direction or in a different direction in which cellulosic biomass solids are being laterally distributed therein. For example, when lateral fluid circulation is used to laterally distribute the cellulosic biomass solids in the hydrothermal digestion unit, the lateral fluid circulation is in the same direction as that of the cellulosic biomass solids. However, when mechanical means, such as a screw impeller, for example, are used to laterally distribute the cellulosic biomass solids in the hydrothermal digestion unit, the lateral fluid circulation may be in the same direction or in the opposite direction to which the cellulosic biomass solids are being laterally distributed.

In some embodiments, the biomass conversion systems may further comprise a biomass feed mechanism that is operatively coupled to the hydrothermal digestion unit, where the biomass feed mechanism is configured for addition of cellulosic biomass solids to the hydrothermal digestion unit while it is in a pressurized state (e.g., at least about 30 bar). Inclusion of the biomass feed mechanism may allow cellulosic biomass solids to be continuously or semi-continuously fed to the hydrothermal digestion unit, thereby allowing hydrothermal digestion to take place in a continual manner by replenishing cellulosic biomass solids that have been digested to form soluble carbohydrates. Suitable biomass feed mechanisms are described in greater detail hereinafter. Without the ability to introduce fresh cellulosic biomass solids to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Techniques through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned US20130152457 and US20130152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner Pressurization may take place via addition of a gas or a liquid to the pressurization zone. In some embodiments, a liquid being used for pressurization may comprise a fluid phase that is transferred from the hydrothermal digestion unit. In other embodiments, instead of being recirculated to the hydrothermal digestion unit, a fluid phase may be diverted to the pressurization zone to affect its pressurization.

Various exemplary embodiments of the biomass conversion systems will now be further described with reference to the drawings. When like elements are used in one or more figures, identical reference characters will be used in each figure, and a detailed description of the element will be provided only at its first occurrence. Some features of the biomass conversion systems may be omitted in certain depicted configurations in the interest of clarity. Moreover, certain features such as, but not limited to, pumps, valves, gas bleeds, gas inlets, fluid inlets, fluid outlets and the like have not necessarily been depicted in the figures, but their presence and function will be understood by one having ordinary skill in the art. In the figures, arrows have been drawn to depict the direction of liquid or gas flow. Moreover, gas transfer lines have been depicted in the figures as single lines, and liquid transfer lines have been depicted as conduits having two sides.

FIGS. 1-4 show schematics of illustrative biomass conversion systems 101, 102, 103 and 104 containing horizontally configured hydrothermal digestion unit 2. As discussed herein, hydrothermal digestion unit 2 has a length or width that is greater than its height. Solids introduction mechanism 4 may be operatively coupled to hydrothermal digestion unit 2, for example, to a top surface thereof. Solids introduction mechanism 4 may comprise loading mechanism 6 and pressure transition zone 8, which may elevate cellulosic biomass solids from atmospheric pressure to a pressure near that of the operating pressure of hydrothermal digestion unit 2, thereby allowing continuous or semi-continuous introduction of cellulosic biomass solids to take place without fully depressurizing hydrothermal digestion unit 2. Pressure isolation may be achieved with valves 10 and 10', which are operable for dispensation of cellulosic biomass solids therethrough. Suitable loading mechanisms and pressure transition zones have been described in more detail hereinabove. Although FIG. 1 has depicted one solids introduction mechanism 4 that is operatively coupled to hydrothermal digestion unit 2, it is to be recognized that more than one solids introduction mechanism 4 may be present, as depicted in FIG. 2. As discussed above, by having multiple solids introduction mechanisms 4 laterally distributed along the top surface of hydrothermal digestion unit 2, there may be a reduced need to laterally distribute the cellulosic biomass solids once they are introduced to hydrothermal digestion unit 2. Moreover, the placement of solids introduction mechanism 4 in the figures is to be considered arbitrary. It is to be recognized that solids introduction mechanism 4 may be centrally located on hydrothermal digestion unit 2 or laterally offset as depicted in FIG. 4. By laterally offsetting solids introduction mechanism 4, the effective contact pathlength of the cellulosic biomass solids in hydrothermal digestion unit 2 may be increased.

Figure 3:
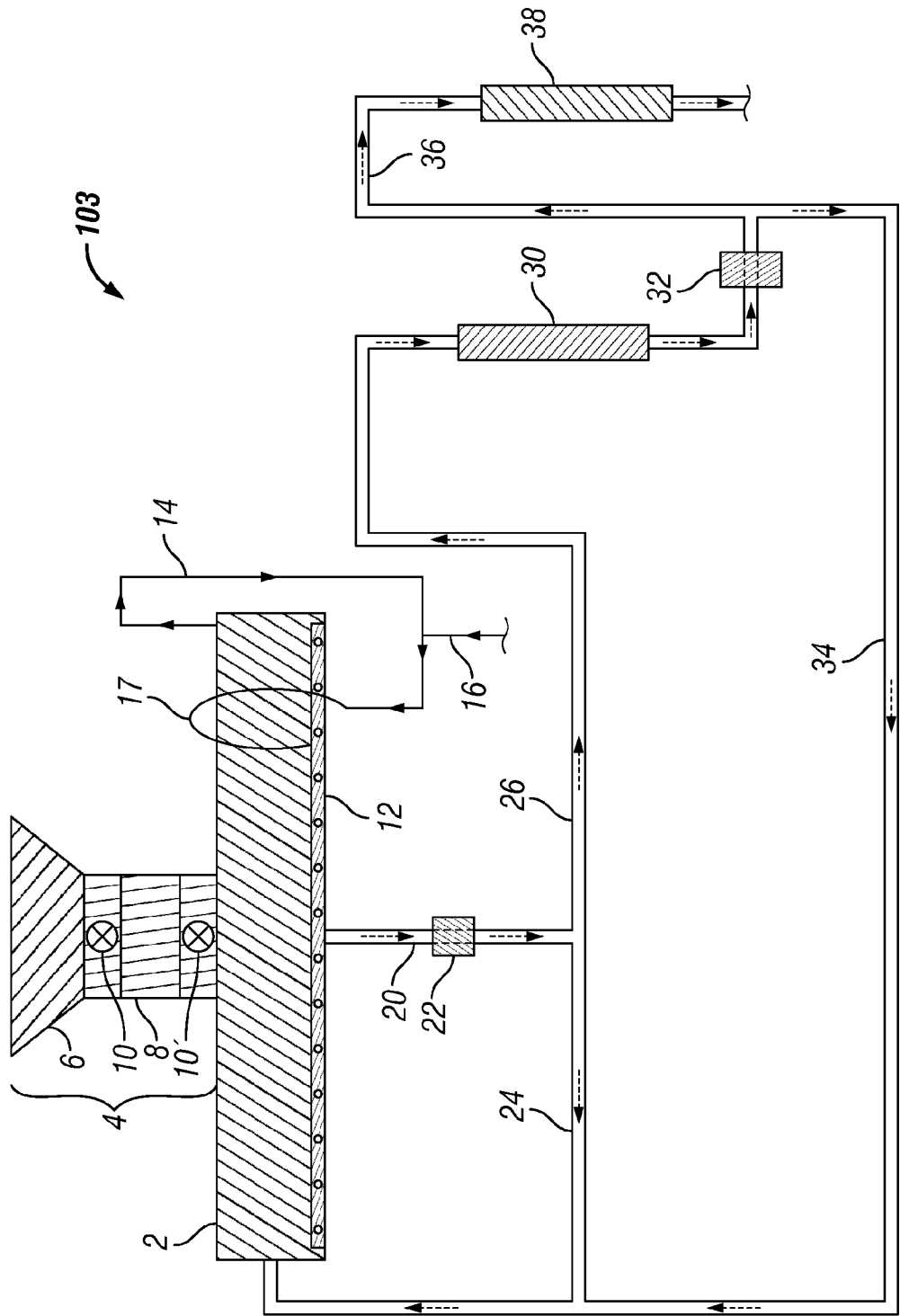

With continued reference to FIGS. 1-4, there may be laterally disposed along the length of hydrothermal digestion unit 2 a gas distribution mechanism 12, which may be configured to form gas bubbles in a fluid phase digestion medium contained therein. Upwardly directed gas flow (e.g., molecular hydrogen) in hydrothermal digestion unit 2 may be supplied by gas distribution mechanism 12. Gas distribution mechanism 12 may be fluidly connected to gas recycle line 14, which may recirculate a gas from a headspace of hydrothermal digestion unit 2 to the bottom of hydrothermal digestion unit 2 by way of gas distribution mechanism 12. Initial gas introduction or supplemental gas introduction to hydrothermal digestion unit 2 may be made via line 16. Although line 16 has been depicted as being fluidly connected to gas recycle line 14, it is to be recognized that line 16 may also be directly fluidly coupled with gas distribution mechanism 12, if desired. As depicted in FIG. 3, gas recycle line 14 may optionally be configured such that it supplies gas from above gas distribution mechanism 12 via dropdown line 17. Benefits of supplying gas to gas distribution mechanism 12 in the manner depicted in FIG. 3 have been discussed in more detail hereinabove.

Referring still to FIGS. 1-4, fluid removal line 20 may be fluidly coupled to hydrothermal digestion unit 2 and optionally contain separations unit 22. Fluid removal line 20 may be used to remove any fluid phase from hydrothermal digestion unit 2. Optional separations unit 22 may, for example, be used to separate a phenolics liquid phase from the fluid phase digestion medium, which contains an alcoholic component formed from cellulosic biomass solids. Separations unit 22 may employ any liquid-liquid or liquid-solid separation technique known to one having ordinary skill in the art. A fluid exiting separations unit 22 may be returned to hydrothermal digestion unit 2 via line 24 or be removed therefrom via line 26 for further processing. In the interest of simplicity, the FIGURES have depicted a single line exiting separations unit 22 and splitting into lines 24 and 26, but it is to be recognized that depending on the type of separation being performed and the eventual destination of the component being separated, multiple lines may emanate from separations unit 22. Fluid being returned to hydrothermal digestion unit 2 via line 24 may include any fluid phase present or formed during the hydrothermal digestion of cellulosic biomass solids, and the return fluid flow may be used to establish a lateral fluid circulation in hydrothermal digestion unit 2. Moreover, slurry catalyst may be returned to hydrothermal digestion unit 2 in the return fluid flow. Although not depicted in the FIGURES, in some embodiments, the return flow from line 24 may be further configured to return the fluid to the top of hydrothermal digestion unit 2 (e.g., from above the cellulosic biomass solids contained therein). In doing so, a slurry catalyst in the returned fluid may be delivered to cellulosic biomass solids contained in hydrothermal digestion unit 2 via downward percolation. In some embodiments, the fluid phase digestion medium and slurry catalyst may be conveyed in line 24. In some or other embodiments, a phenolics liquid phase and slurry catalyst accumulated therein may be conveyed in line 24. In some embodiments, supplemental digestion medium may be added to hydrothermal digestion unit 2 in addition to the return fluid flow. In the interest of clarity, the FIGURES have not depicted a line for supplemental digestion medium introduction.

The fluid exiting hydrothermal digestion unit 2 via line 20 may comprise a fluid phase digestion medium, which may contain an alcoholic component derived from cellulosic biomass solids. The alcoholic component may be further processed by the remaining components of the biomass conversion system. Optionally, polishing reactor 30 may be fluidly coupled to hydrothermal digestion unit 2 via line 26. Polishing reactor 30 may contain a catalyst capable of activating molecular hydrogen, such that soluble carbohydrates being conveyed from hydrothermal digestion unit 2 may be further converted into an alcoholic component or the degree of oxygenation of the alcoholic component may be further decreased. Although not depicted in the FIGURES, an additional feed of molecular hydrogen may be supplied to polishing reactor 30. For example, in some embodiments, a glycol may be converted into a monohydric alcohol in polishing reactor 30. The catalyst present in polishing reactor 30 may be the same as or different than the slurry catalyst present in hydrothermal digestion unit 2. Thereafter, the alcoholic component may be conveyed to separations unit 32, where various operations may take place. Again, any suitable liquid-liquid separation technique known in the art may be employed in separations unit 32. In the interest of simplicity, the FIGURES have depicted a single line exiting separations unit 32 and splitting into lines 34 and 36, but it is to be recognized that depending on the type of separation being performed and the eventual destination of the component being separated, multiple lines may emanate from separations unit 32. In some embodiments, at least a portion of any water present in the alcoholic component may be removed in separations unit 32 before subsequent downstream processing takes place. In some embodiments, a phenolics liquid phase may be separated from the alcoholic component in separations unit 32 before further processing takes place, or the viscosity of the phenolics liquid phase may be reduced by at least partially depolymerizing the lignin therein (e.g., via thermal depolymerization). In some embodiments, a portion of the alcoholic component may be separated from the remainder of the liquid phase being processed in separations unit 32. Optionally, at least a portion of the separated alcoholic component may be recirculated to hydrothermal digestion unit 2 via recycle line 34, which is fluidly coupled to line 24, if desired.

The alcoholic component exiting separations unit 32 may be conveyed to reforming reactor 38 via line 36. In reforming reactor 38, a condensation reaction or other reforming reaction may take place. The reforming reaction taking place therein may be catalytic or non-catalytic. Although only one reforming reactor 38 has been depicted in FIGS. 1-4, it is to be understood that any number of reforming reactors 38 may be present. In reforming reactor 38, one or more further reforming reactions may take place, as described above. In some embodiments, a first reforming reaction may comprise a condensation reaction. Additional reforming reactions may comprise any combination of further catalytic reduction reactions (e.g., hydrogenation reactions, hydrogenolysis reactions, hydrotreating reactions, and the like), further condensation reactions, isomerization reactions, desulfurization reactions, dehydration reactions, oligomerization reactions, alkylation reactions, and the like. Such transformations may be used to convert the initially produced soluble carbohydrates into a biofuel. Such biofuels may include, for example, gasoline hydrocarbons, diesel fuels, jet fuels, and the like. As used herein, the term "gasoline hydrocarbons" refers to substances comprising predominantly $C_5$-$C_9$ hydrocarbons and having a boiling point of 32° C. to about 204° C. More generally, any fuel blend meeting the requirements of ASTM D2887 may be classified as a gasoline hydrocarbon. Suitable gasoline hydrocarbons may include, for example, straight run gasoline, naphtha, fluidized or thermally catalytically cracked gasoline, VB gasoline, and coker gasoline. As used herein, the term "diesel fuel" refers to substances comprising paraffinic hydrocarbons and having a boiling point ranging between about 187° C. and about 417° C., which is suitable for use in a compression ignition engine. More generally, any fuel blend meeting the requirements of ASTM D975 may also be defined as a diesel fuel. As used herein, the term "jet fuel" refers to substances meeting the requirements of ASTM D1655. In some embodiments, jet fuels may comprise a kerosene-type fuel having substantially $C_8$-$C_{16}$ hydrocarbons (Jet A and Jet A-1 fuels). In other embodiments, jet fuels may comprise a wide-cut or naphtha-type fuel having substantially $C_5$-$C_{15}$ hydrocarbons present therein (Jet B fuels).

As described in more detail above, cellulosic biomass solids being introduced to hydrothermal digestion unit 2 may become laterally distributed therein by floating on a fluid phase and/or by being conveyed by a circulating fluid phase. As also described hereinabove, the cellulosic biomass solids may also become mechanically distributed in hydrothermal digestion unit 2 by way of a solids transport mechanism. Referring to FIG. 4, biomass conversion system 104 is depicted in which screw impeller 40 may be used to laterally distribute cellulosic biomass solids from one end of hydrothermal digestion unit 2 to the other. It should be noted that in FIG. 4, solids introduction mechanism 4 has been laterally offset to one side of hydrothermal digestion unit 2 in order to increase the effective pathlength of cellulosic biomass solids therein. It is to be recognized, however, that other locations of solids introduction are possible, and the configuration depicted in FIG. 4 should not be considered as limiting.

As discussed above, multiple hydrothermal digestion units may fluidly connected to one another in series in accordance with the embodiments described herein. Although a first hydrothermal digestion unit fluidly connected in series to another hydrothermal digestion unit may be oriented in a horizontal configuration, subsequent hydrothermal digestion units fluidly connected to the first hydrothermal digestion unit need not necessarily be so configured. As discussed above, subsequent hydrothermal digestion units may be vertically configured or horizontally configured, and various types of fluid couplings may be established between the digestion units.

FIGS. 5-11 show schematics of illustrative biomass conversion systems 105, 106, 107, 108, 109, 110 and 111 containing a horizontally configured hydrothermal digestion unit 2 and another hydrothermal digestion unit 2' fluidly connected thereto. As discussed above, the fluid connection between hydrothermal digestion units 2 and 2' may take place in various ways and with varying configurations of hydrothermal digestion unit 2'.

Figure 5:
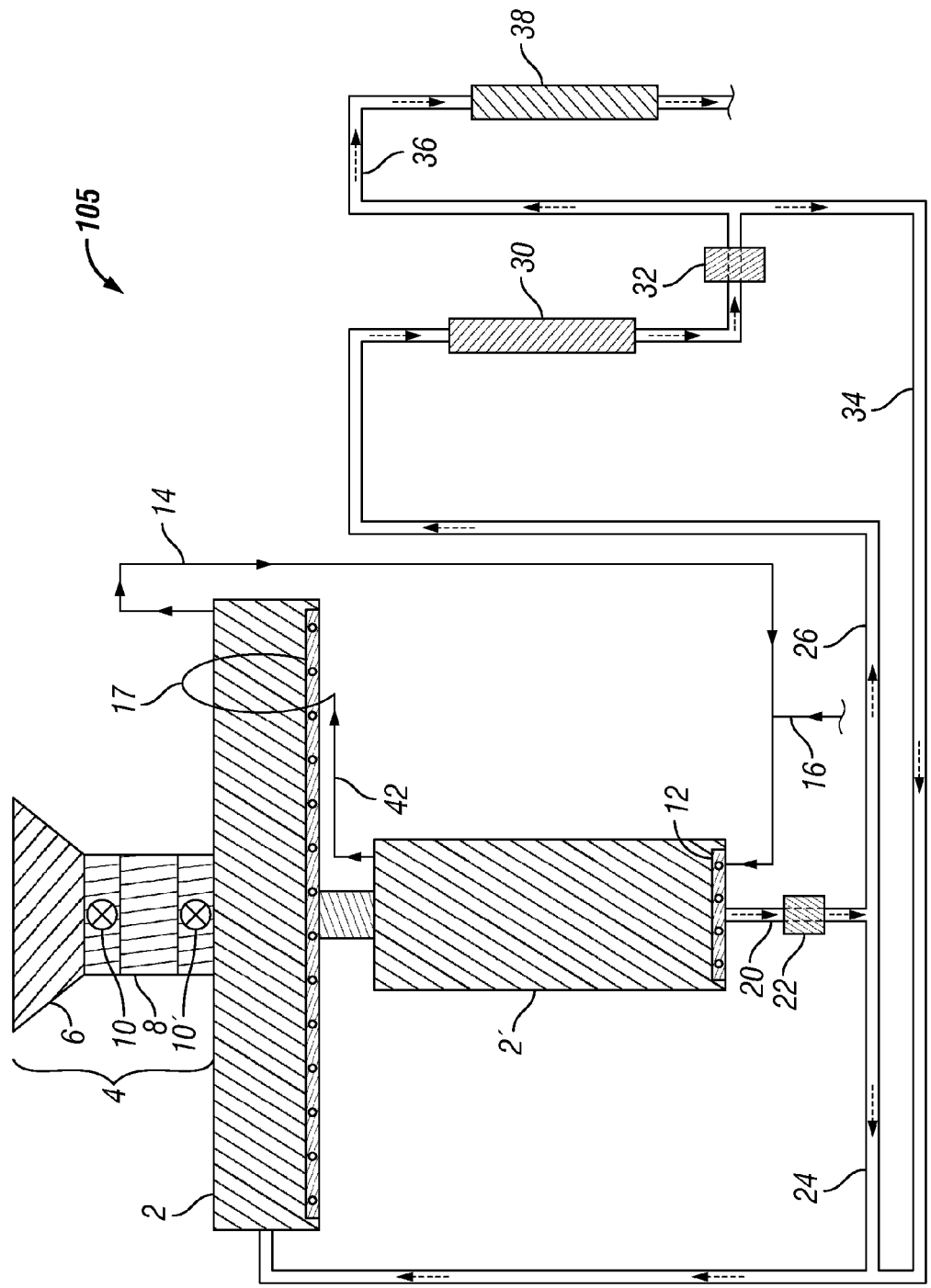
FIGS. 5-11 show schematics of illustrative biomass conversion systems containing a horizontally configured hydrothermal digestion unit and another hydrothermal digestion unit fluidly connected thereto.
Figure 6:
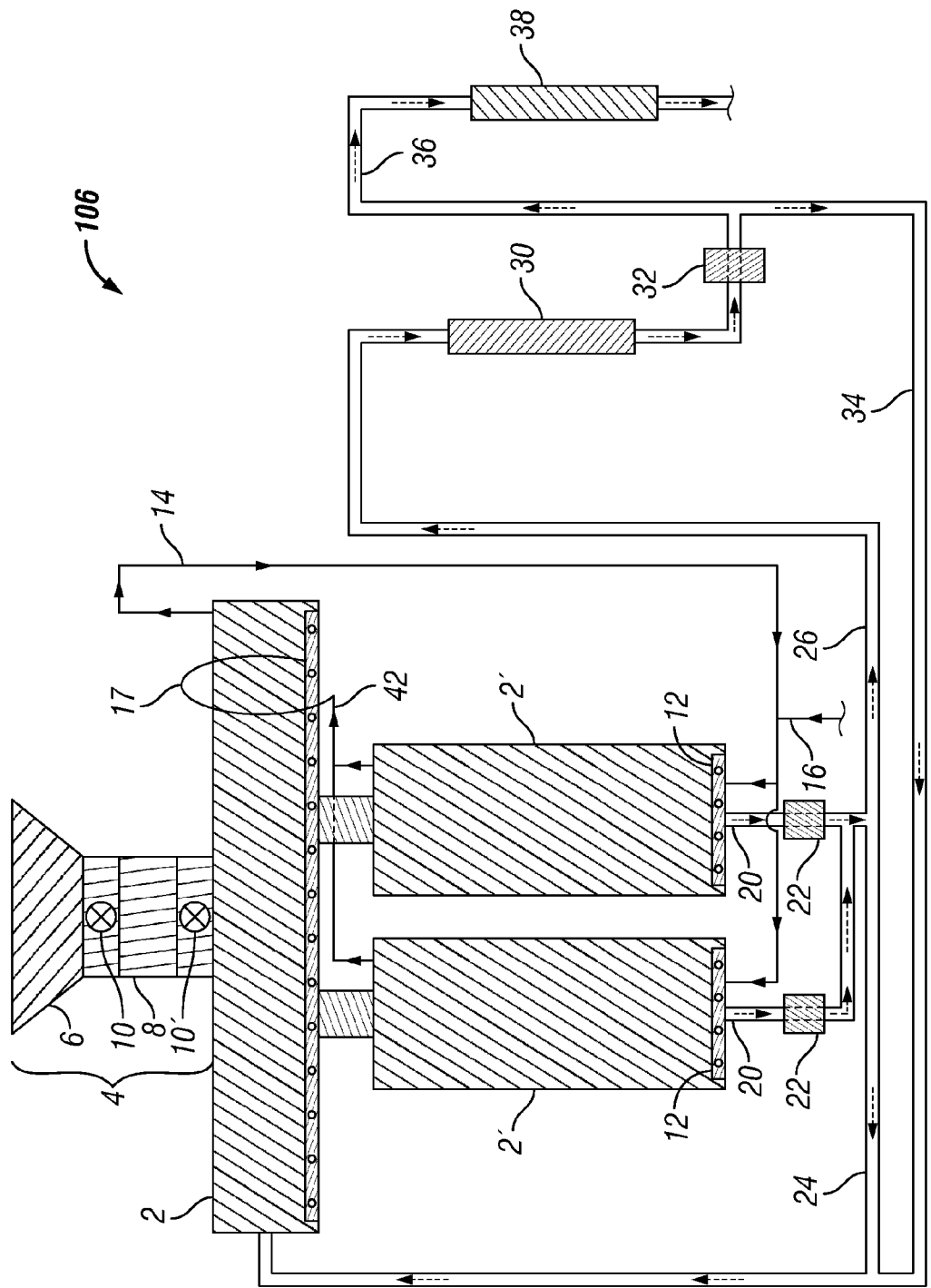

In FIG. 5, hydrothermal digestion unit 2 is in a horizontal configuration and hydrothermal digestion unit 2' is in a vertical configuration, where the bottom of hydrothermal digestion unit 2 is fluidly connected to the top of hydrothermal digestion unit 2'. As depicted in FIG. 6, multiple vertically configured hydrothermal digestion units 2' may be fluidly connected in parallel to hydrothermal digestion unit 2 in a similar manner. As depicted in FIGS. 5 and 6, a gas (e.g., molecular hydrogen) may be recirculated from a headspace of hydrothermal digestion unit 2 to gas distribution mechanism 12 in hydrothermal digestion unit 2'. Gas circulation to hydrothermal digestion unit 2 from hydrothermal digestion unit 2' may be supplied via gas recycle line 42 by way of dropdown line 17. The remaining elements depicted in FIGS. 5 and 6 operate in a similar manner to that described in more detail above and will not be described again in detail.

Figure 7:
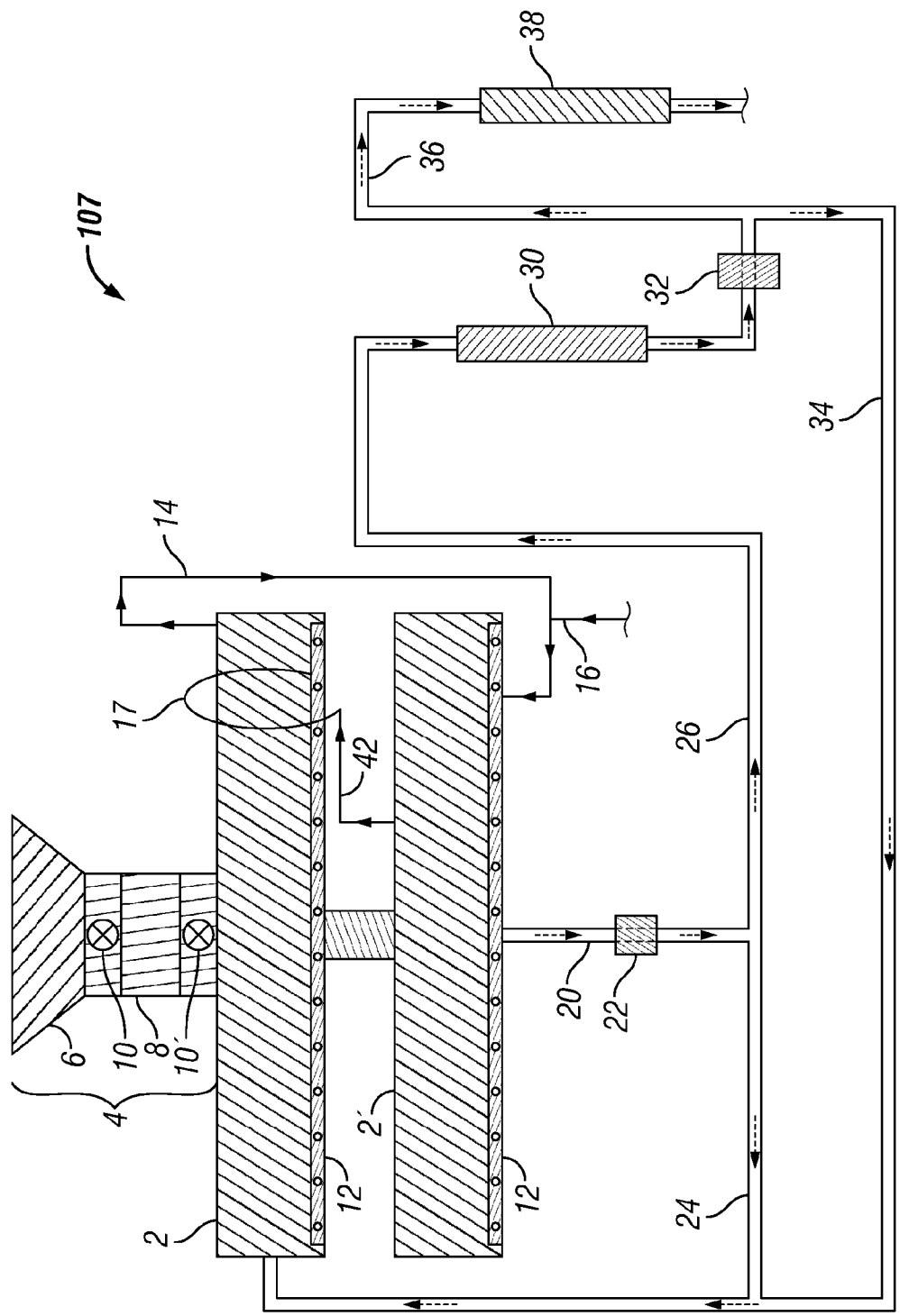
Figure 8:
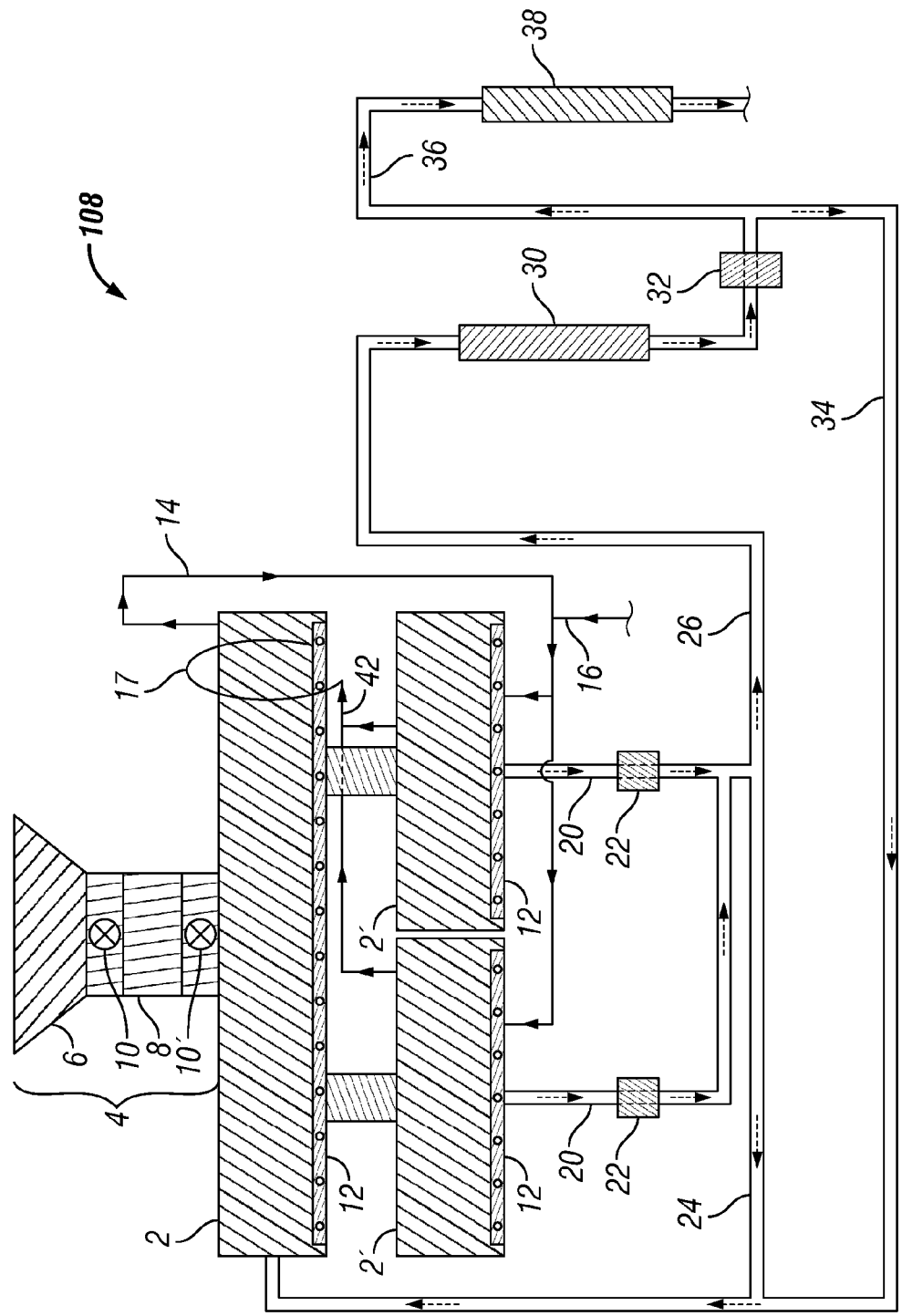
Figure 9:
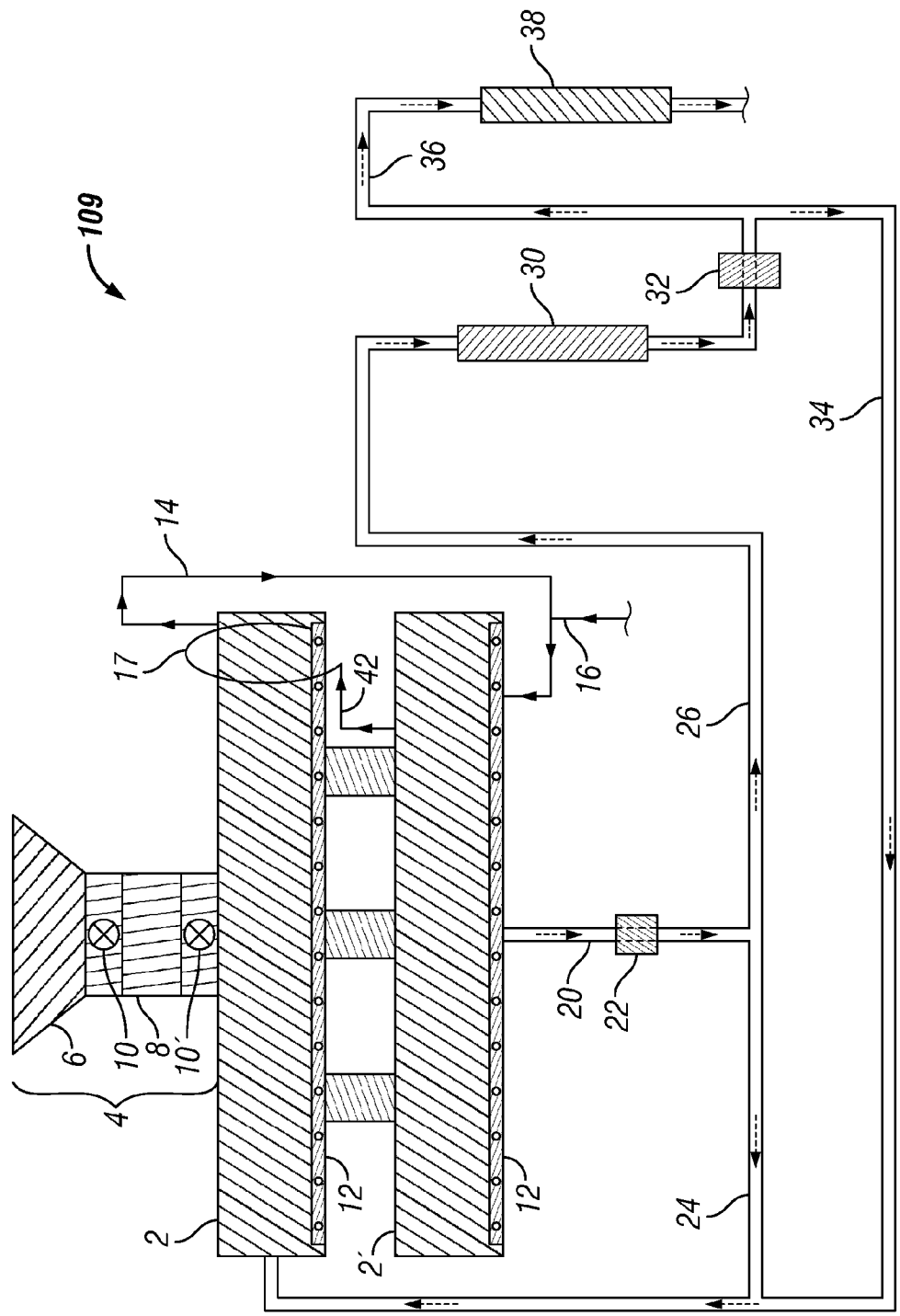
Figure 10:
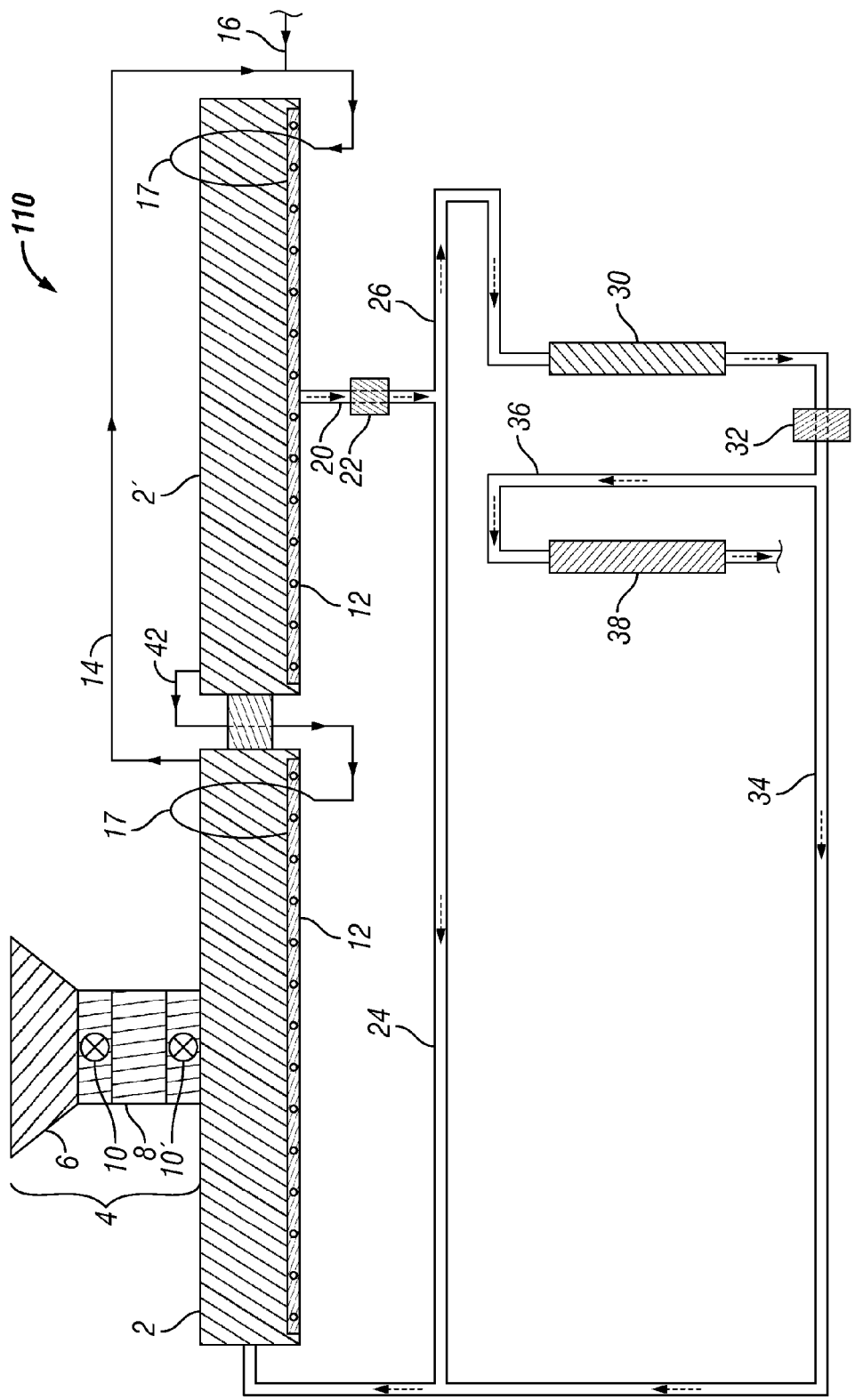
Figure 11:
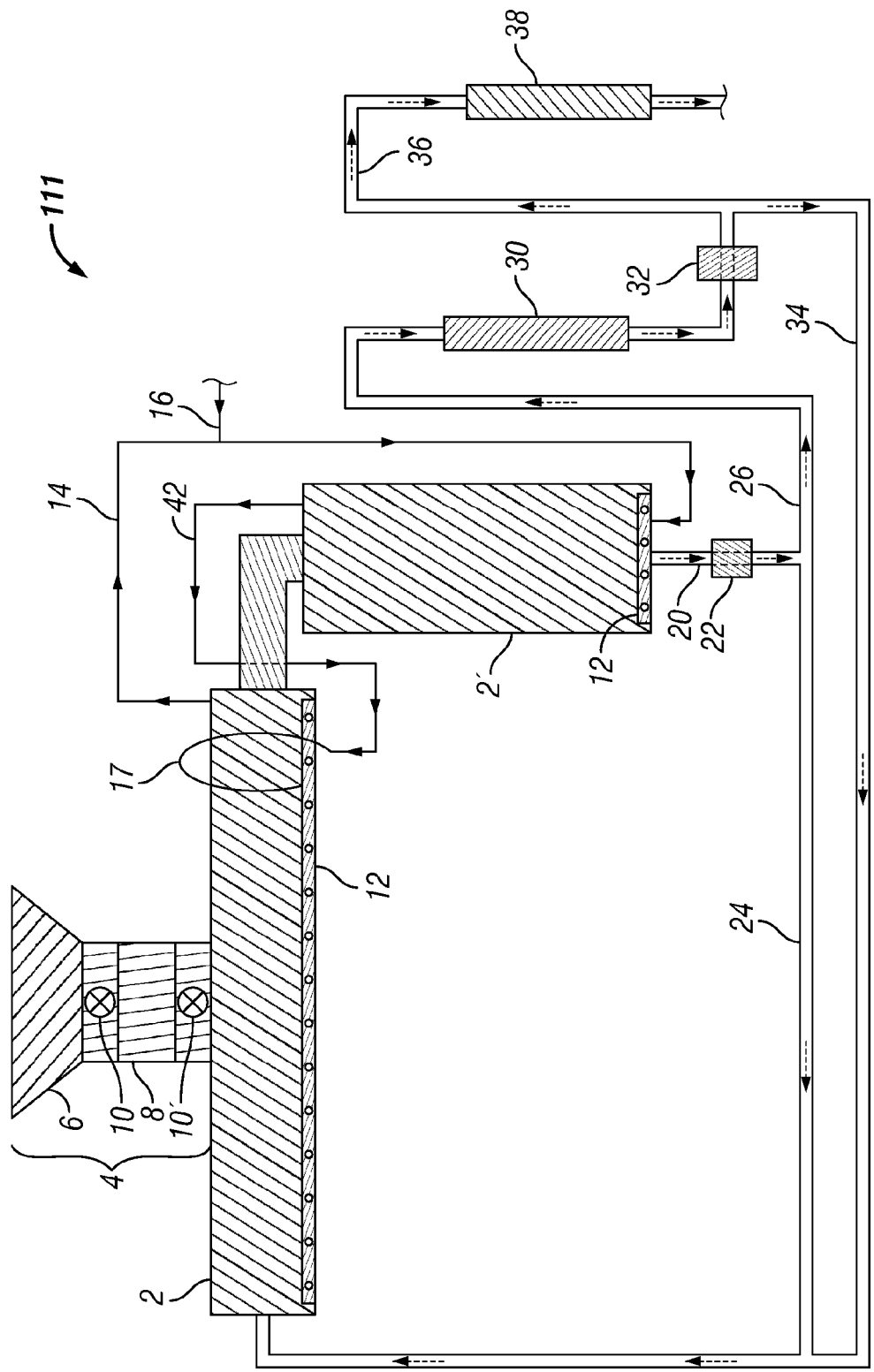

In FIG. 7, hydrothermal digestion unit 2 is in a horizontal configuration and hydrothermal digestion unit 2' is also in a horizontal configuration, where the bottom of hydrothermal digestion unit 2 is connected to the top of hydrothermal digestion unit 2'. Again, multiple hydrothermal digestion units 2' may be fluidly connected to hydrothermal digestion unit 2, as depicted in FIG. 8. Moreover, multiple fluid connections may be made between hydrothermal digestion units 2 and 2' as depicted in FIG. 9. Hydrothermal digestion units 2 and 2' may also be fluidly connected to one another end-to-end, as depicted in FIGS. 10 and 11. In FIG. 10, hydrothermal digestion unit 2' is in a horizontal configuration, and in FIG. 11, hydrothermal digestion unit 2' is in a vertical orientation. Again, the remaining elements depicted in FIGS. 7-11 operate in a similar manner to that described in more detail above and will not be described again in detail.

Figure 12:
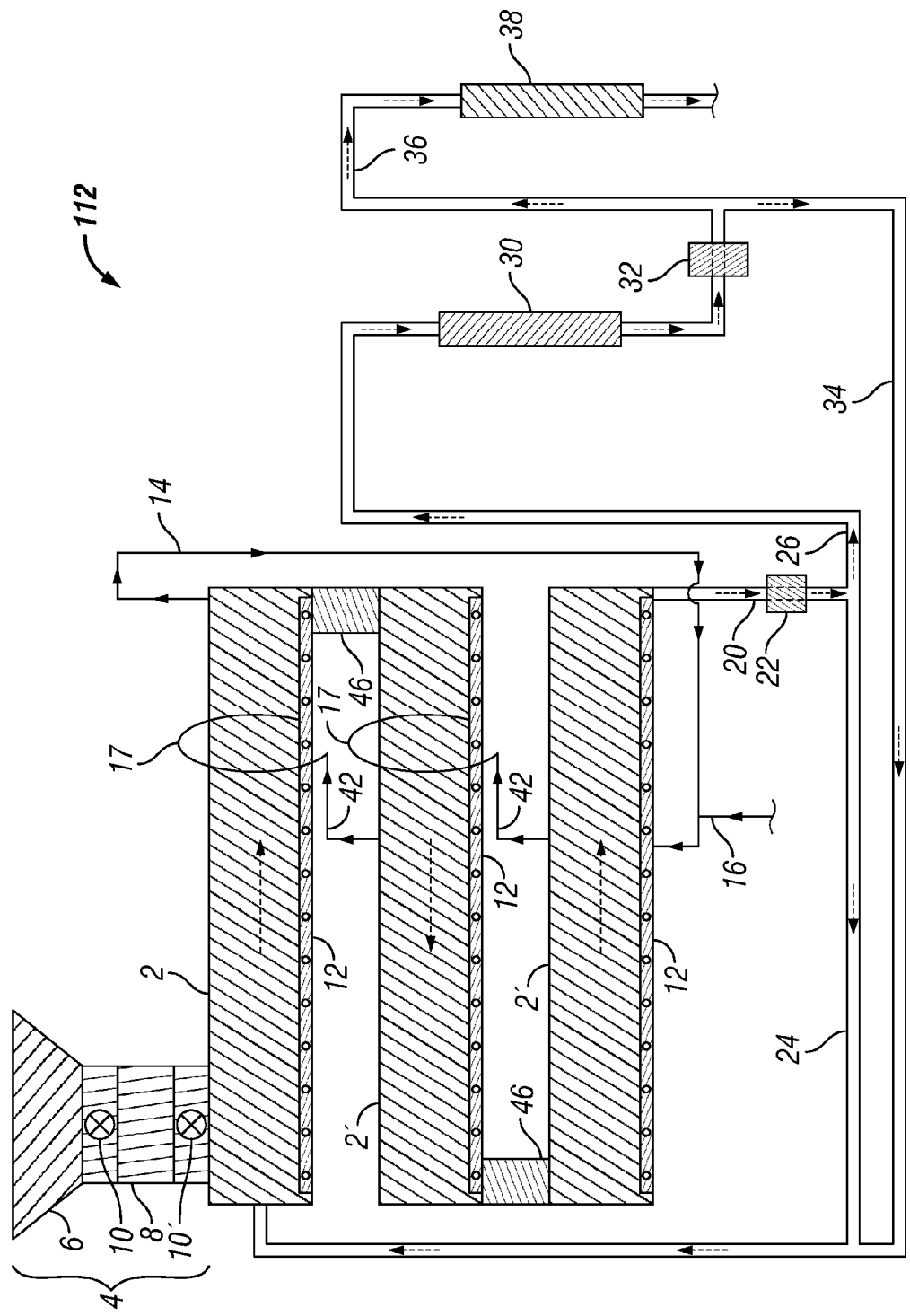
FIG. 12 shows a schematic of an illustrative biomass conversion system containing a horizontally configured hydrothermal digestion unit and multiple hydrothermal digestion units fluidly coupled thereto and vertically spaced apart therefrom, where fluid circulation is used to laterally distribute cellulosic biomass solids.

FIG. 12 shows a schematic of an illustrative biomass conversion system 112 containing horizontally configured hydrothermal digestion unit 2 and multiple hydrothermal digestion units 2' fluidly coupled thereto and vertically spaced apart therefrom, where fluid circulation is used to laterally distribute cellulosic biomass solids within hydrothermal digestion units 2 and 2'. The direction of fluid circulation within hydrothermal digestion units 2 and 2' is indicated with dashed arrows. As depicted in FIG. 12, solids introduction mechanism 4 is laterally offset on hydrothermal digestion unit 2, such that the effective contacting pathlength for cellulosic biomass solids in hydrothermal digestion unit 2 corresponds to its elongated dimension. Once the cellulosic biomass solids have laterally traversed hydrothermal digestion unit 2, they may drop via gravity by way of vertical fluid connection 46 to the next fluidly connected hydrothermal digestion unit 2' and then be laterally carried therethrough by fluid circulation. This process may continue until the cellulosic biomass solids reach the bottom hydrothermal digestion unit 2' and the cellulosic biomass solids become completely digested. Fluid recirculation and downstream processing may take place substantially as described above for FIGS. 1-11.

In further regard to the methods described herein, the processing of cellulosic biomass solids to produce an alcoholic component will now be described in greater detail with reference to FIGS. 1-4. Although the description that follows is directed processing of cellulosic biomass solids within biomass conversion systems containing a single horizontally configured hydrothermal digestion unit, it is to be recognized that like transformations may take place in biomass conversion systems containing multiple hydrothermal digestion units that are fluidly coupled to one another, such as those depicted in FIGS. 5-12. For example, in biomass conversion systems containing multiple hydrothermal digestion units that are fluidly connected to one another, hydrothermal digestion to produce partially digested cellulosic biomass solids may occur in a first hydrothermal digestion unit, and those partially digested cellulosic biomass solids may then be conveyed to a second hydrothermal digestion unit, where the digestion process may be subsequently completed. Moreover, hydrothermal digestion may be conducted at different temperatures in the first and second hydrothermal digestion units. For example, hydrothermal digestion in the first hydrothermal digestion unit to produce partially digested cellulosic biomass solids may take place at a lower temperature than does the hydrothermal digestion that takes place in the second hydrothermal digestion unit.

Referring to FIGS. 1-4, cellulosic biomass solids may be introduced from loading mechanism 6 to pressurization zone 8, where they may be elevated from atmospheric pressure to an elevated pressure that is present within hydrothermal digestion unit 2. After pressurization, valve 10' located between pressurization zone 8 and hydrothermal digestion unit 2 may be opened such that the cellulosic biomass solids drop via gravity into hydrothermal digestion unit 2. Once the cellulosic biomass solids are in hydrothermal digestion unit 2, they may become laterally distributed therein. In some embodiments, the cellulosic biomass solids may float on a fluid phase digestion medium located within hydrothermal digestion unit 2, before the cellulosic biomass solids eventually become saturated with the fluid phase digestion medium and sink. Lateral distribution of the cellulosic biomass solids within hydrothermal digestion unit 2 may also be aided by introducing the cellulosic biomass solids from multiple solids introduction mechanisms 4, as depicted in FIG. 2. Likewise, lateral distribution of the cellulosic biomass solids within hydrothermal digestion unit 2 may be aided by screw impeller 40, as depicted in FIG. 4. After or while the cellulosic biomass solids are being laterally distributed in hydrothermal digestion unit 2, molecular hydrogen may be distributed in the cellulosic biomass solids via upwardly directed flow from gas distribution mechanism 12. The upwardly directed flow of molecular hydrogen may fluidize slurry catalyst particulates also present in hydrothermal digestion unit 2, such that they also become distributed in the cellulosic biomass solids.

Molecular hydrogen may be recirculated through hydrothermal digestion unit 2 via gas recycle line 14. Initial molecular hydrogen introduction and/or supplementation of the circulating molecular hydrogen may be provided via line 16. Although line 16 has been depicted as introducing startup or supplemental molecular hydrogen at the same location as the recirculated molecular hydrogen, it is to be recognized that this need not necessarily be the case. Recirculation of molecular hydrogen via gas recycle line 14 may allow molecular hydrogen that has passed completely through a given portion of cellulosic biomass solids and formed a continuous gas phase thereabove to be returned to the cellulosic biomass solids. While in a continuous gas phase above the cellulosic biomass solids, the molecular hydrogen may no longer be effective for stabilizing soluble carbohydrates in a fluid phase digestion medium via a catalytic reduction reaction, since the molecular hydrogen is no longer distributed in the cellulosic biomass solids. Hence, return of the molecular hydrogen to the cellulosic biomass solids may be desirable to better promote the stabilization of soluble carbohydrates and decrease the needed input of additional molecular hydrogen. As depicted in FIG. 3, molecular hydrogen may be supplied to gas distribution system 12 via dropdown line 17, which may be a desirable configuration for preventing incursion of the fluid phase digestion medium and/or solids into gas distribution mechanism 12.

The various fluid components present or formed in hydrothermal digestion unit 2 may be removed via line 20. Optionally, the components may be separated in separations unit 22, such as, for example, to separate the fluid phase digestion medium from a phenolics liquid phase. The original fluid phase or a separated fluid phase may be returned to hydrothermal digestion unit 2 via line 24. The slurry catalyst may also be returned to hydrothermal digestion unit 2 with the return flow in line 24, where it may continue to be employed in the hydrothermal digestion process. In addition to returning the slurry catalyst to hydrothermal digestion unit 2, the return flow from line 24 may establish lateral fluid circulation therein. As described above, the lateral fluid circulation may further promote the lateral distribution of cellulosic biomass solids in hydrothermal digestion unit 2.

The original fluid phase or a separated fluid phase that is not being returned to hydrothermal digestion unit 2 may be conveyed by line 26 and further processed. The fluid phase being conveyed by line 26 may contain an alcoholic component derived from the cellulosic biomass solids. Optionally, the alcoholic component contained in the fluid phase may be further formed in polishing reactor 30 and/or the degree of oxygenation of the alcoholic component may be further decreased therein. Optionally thereafter, the alcoholic component may undergo further separation in separations unit 32, such as removing at least a portion of any water present from the fluid phase prior to conveying the alcoholic component to reforming reactor 38. Further optionally, at least a portion of the alcoholic component may be returned to hydrothermal digestion unit 2 by way of line 34 after separation. Particular benefits of returning a separated alcoholic component to hydrothermal digestion unit 2 may include, for example, maintaining a clean catalyst surface for better promoting the stabilization of soluble carbohydrates. Finally, the alcoholic component may undergo a condensation reaction or other reforming reaction in reforming reactor 38 in the process of being transformed into a biofuel.

As further discussed above, methods described herein may further comprise removing at least a portion of the fluid phase digestion medium and the slurry catalyst from the hydrothermal digestion unit, after the alcoholic component has been formed. In some embodiments, the methods described herein may further comprise returning at least a portion of the fluid phase digestion medium and the slurry catalyst to the hydrothermal digestion unit. As discussed above, returning the fluid phase digestion medium and the slurry catalyst to the hydrothermal digestion unit may allow hydrothermal digestion to continue unabated and promote the lateral distribution of cellulosic biomass solids in the hydrothermal digestion unit via lateral fluid circulation. In some embodiments, the fluid phase digestion medium and the slurry catalyst may be circulated laterally through the hydrothermal digestion unit in the same direction in which the cellulosic biomass solids are being laterally distributed in the hydrothermal digestion unit. That is, in such embodiments, the fluid phase digestion medium and the slurry catalyst may be circulated in a co-flow manner with the cellulosic biomass solids. However, it is to be recognized that countercurrent return flow may be desirable in some embodiments. Specifically, in some embodiments, the fluid phase digestion medium and the slurry catalyst may be circulated laterally within the hydrothermal digestion unit in the opposite direction in which the cellulosic biomass solids are being laterally distributed in the hydrothermal digestion unit. When multiple hydrothermal digestion units are present, the fluid phase digestion medium and the slurry catalyst may be circulated from a second hydrothermal digestion unit to a first hydrothermal digestion unit in order to establish a fluid circulation loop therebetween.

As further described above in reference to the drawings, the methods described herein may further comprise recirculating molecular hydrogen during the hydrothermal digestion of cellulosic biomass solids. When multiple hydrothermal digestion units are present, at least a portion of the molecular hydrogen may be recirculated within the same hydrothermal digestion unit or between different hydrothermal digestion units. Specifically, in some embodiments, methods described herein may further comprise recirculating at least a portion of the molecular hydrogen from a headspace of either hydrothermal digestion unit to the same hydrothermal digestion unit or a different hydrothermal digestion unit, where the molecular hydrogen may be recirculated to a source of upwardly directed fluid flow therein (e.g., a gas distribution mechanism).

Further discussion of the transformations that take place on the cellulosic biomass solids in the hydrothermal digestion unit and thereafter are now described in greater detail. In various embodiments, the alcoholic component derived from the cellulosic biomass solids may be formed by a catalytic reduction reaction of soluble carbohydrates, where the soluble carbohydrates are derived from the cellulosic biomass solids. As described above, the methods and systems set forth herein can help promote adequate distribution of the slurry catalyst and the molecular hydrogen throughout the cellulosic biomass solids such that the catalytic reduction reaction can more effectively take place.

In some embodiments, the catalytic reduction reaction used to produce the alcoholic component may take place at a temperature ranging between about 110° C. and about 300° C., or between about 170° C. and about 300° C., or between about 180° C. and about 290° C., or between about 150° C. and about 250° C. In some embodiments, the catalytic reduction reaction used to produce the alcoholic component may take place at a pH ranging between about 7 and about 13, or between about 10 and about 12. In other embodiments, the catalytic reduction reaction may take place under acidic conditions, such as at a pH of about 5 to about 7. Acids, bases, and buffers may be introduced as necessary to achieve a desired pH level. In some embodiments, the catalytic reduction reaction may be conducted under a hydrogen partial pressure ranging between about 1 bar (absolute) and about 150 bar, or between about 15 bar and about 140 bar, or between about 30 bar and about 130 bar, or between about 50 bar and about 110 bar.

In various embodiments, the fluid phase digestion medium in which the hydrothermal digestion and catalytic reduction reaction are conducted may comprise an organic solvent and water. Although any organic solvent that is at least partially miscible with water may be used as a digestion solvent, particularly advantageous organic solvents are those that can be directly converted into fuel blends and other materials without being separated from the alcoholic component being produced from the cellulosic biomass solids. That is, particularly advantageous organic solvents are those that may be co-processed along with the alcoholic component during downstream reforming reactions into fuel blends and other materials. Suitable organic solvents in this regard may include, for example, ethanol, ethylene glycol, propylene glycol, glycerol, and any combination thereof.

In some embodiments, the fluid phase digestion medium may further comprise a small amount of a monohydric alcohol. The presence of at least some monohydric alcohols in the fluid phase digestion medium may desirably enhance the hydrothermal digestion and/or the catalytic reduction reactions being conducted therein. For example, inclusion of about 1% to about 5% by weight monohydric alcohols in the fluid phase digestion medium may desirably maintain catalyst activity due to a surface cleaning effect. Monohydric alcohols present in the digestion solvent may arise from any source. In some embodiments, the monohydric alcohols may be formed via the in situ catalytic reduction reaction process being conducted therein. In some or other embodiments, the monohydric alcohols may be formed during further chemical transformations of the initially formed alcoholic component. In still other embodiments, the monohydric alcohols may be sourced from an external feed that is in flow communication with the cellulosic biomass solids.

In some embodiments, the fluid phase digestion medium may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the fluid phase digestion medium may comprise about 90% or less water by weight. In other embodiments, the fluid phase digestion medium may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

In some embodiments, the catalyst that is capable of activating molecular hydrogen may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen are described in commonly owned US20120317872 and US20130109896, each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst, such as a catalyst comprising about 1-10 wt. % cobalt oxide and up to about 30 wt. % molybdenum trioxide. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in U.S. Patent Application Publication No. 20100236988 and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalysts. Catalyst fines may also be produced by grinding larger catalyst solids or during regeneration of catalyst solids. Suitable methods for producing catalyst fines are described in U.S. Pat. Nos. 6,030,915 and 6,127,299, each of which is incorporated herein by reference in its entirety. In some instances, catalyst fines may be intentionally removed from a solid catalyst production run, since they may be difficult to sequester in some catalytic processes. Techniques for removing catalyst fines from larger catalyst solids may include, for example, sieving or like size separation processes. When conducting in situ catalytic reduction reaction processes, such as those described herein, catalyst fines may be particularly well suited, since they can be easily fluidized and distributed in the interstitial pore space of the digesting cellulosic biomass solids.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals.

In some embodiments, the alcoholic component formed from the cellulosic biomass solids may be further reformed into a biofuel. Reforming the alcoholic component into a biofuel or other material may comprise any combination and sequence of further hydrogenolysis reactions and/or hydrogenation reactions, condensation reactions, isomerization reactions, oligomerization reactions, hydrotreating reactions, alkylation reactions, dehydration reactions, desulfurization reactions, and the like. The subsequent reforming reactions may be catalytic or non-catalytic. In some embodiments, an initial operation of downstream reforming may comprise a condensation reaction, often conducted in the presence of a condensation catalyst, in which the alcoholic component or a product derived therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

In some embodiments, methods described herein may further comprise performing a condensation reaction on the alcoholic component or a product derived therefrom. In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. For example, in some embodiments, the product of the condensation reaction may comprise $\geq C_4$ alcohols and/or ketones that are produced concurrently with or in lieu of $\geq C_4$ hydrocarbons. In some embodiments, the $\geq C_4$ hydrocarbons produced by the condensation reaction may contain various olefins in addition to alkanes of various sizes, typically branched alkanes. In still other embodiments, the $\geq C_4$ hydrocarbons produced by the condensation reaction may also comprise cyclic hydrocarbons and/or aromatic compounds. In some embodiments, the higher molecular weight compound produced by the condensation reaction may be further subjected to a catalytic reduction reaction to transform a carbonyl functionality therein to an alcohol and/or a hydrocarbon and to convert olefins into alkanes.

Exemplary compounds that may be produced by a condensation reaction include, for example, $\geq C_4$ alkanes, $\geq C_4$ alkenes, $\geq C_5$ cycloalkanes, $\geq C_5$ cycloalkenes, aryls, fused aryls, $\geq C_4$ alcohols, $\geq C_4$ ketones, and mixtures thereof. The $\geq C_4$ alkanes and $\geq C_4$ alkenes may range from 4 to about 30 carbon atoms (i.e. $C_4$-$C_{30}$ alkanes and $C_4$-$C_{30}$ alkenes) and may be branched or straight chain alkanes or alkenes. The $\geq C_4$ alkanes and $\geq C_4$ alkenes may also include fractions of $C_7$-$C_{14}$, $C_{12}$-$C_{24}$ alkanes and alkenes, respectively, with the $C_7$-$C_{14}$ fraction directed to jet fuel blends, and the $C_{12}$-$C_{24}$ fraction directed to diesel fuel blends and other industrial applications. Examples of various $\geq C_4$ alkanes and $\geq C_4$ alkenes that may be produced by the condensation reaction include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethylhexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $\geq C_5$ cycloalkanes and $\geq C_5$ cycloalkenes may have from 5 to about 30 carbon atoms and may be unsubstituted, mono-substituted or multi-substituted. In the case of mono-substituted and multi-substituted compounds, the substituted group may include a branched $\geq C_3$ alkyl, a straight chain $\geq C_1$ alkyl, a branched $\geq C_3$ alkylene, a straight chain $\geq C_1$ alkylene, a straight chain $\geq C_2$ alkylene, an aryl group, or a combination thereof. In some embodiments, at least one of the substituted groups may include a branched $C_3$-$C_{12}$ alkyl, a straight chain $C_1$-$C_{12}$ alkyl, a branched $C_3$-$C_{12}$ alkylene, a straight chain $C_1$-$C_{12}$ alkylene, a straight chain $C_2$-$C_{12}$ alkylene, an aryl group, or a combination thereof. In yet other embodiments, at least one of the substituted groups may include a branched $C_3$-$C_4$ alkyl, a straight chain $C_1$-$C_4$ alkyl, a branched $C_3$-$C_4$ alkylene, a straight chain $C_1$-$C_4$ alkylene, a straight chain $C_2$-$C_4$ alkylene, an aryl group, or any combination thereof. Examples of $\geq C_5$ cycloalkanes and $\geq C_5$ cycloalkenes that may be produced by the condensation reaction include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

The moderate fractions of the condensation reaction, such as $C_7$-$C_{14}$, may be separated for jet fuel, while heavier fractions, such as $C_{12}$-$C_{24}$, may be separated for diesel use. The heaviest fractions may be used as lubricants or cracked to produce additional gasoline and/or diesel fractions. The $\geq C_4$ compounds may also find use as industrial chemicals, whether as an intermediate or an end product. For example, the aryl compounds toluene, xylene, ethylbenzene, para-xylene, meta-xylene, and ortho-xylene may find use as chemical intermediates for the production of plastics and other products. Meanwhile, $C_9$ aromatic compounds and fused aryl compounds, such as naphthalene, anthracene, tetrahydronaphthalene, and decahydronaphthalene, may find use as solvents or additives in industrial processes.

In some embodiments, a single catalyst may mediate the transformation of the alcoholic component into a form suitable for undergoing a condensation reaction as well as mediating the condensation reaction itself. In other embodiments, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in a fluid.

Various operations may optionally be performed on the alcoholic component prior to conducting a condensation reaction. In addition, various operations may optionally be performed on a fluid phase containing the alcoholic component, thereby further transforming the alcoholic component or placing the alcoholic component in a form more suitable for taking part in a condensation reaction. These optional operations are now described in more detail below.

As described above, one or more liquid phases may be present when digesting cellulosic biomass solids. Particularly when cellulosic biomass solids are fed continuously or semi-continuously to the hydrothermal digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to a location above the cellulosic biomass solids and releasing them, thereby allowing the slurry catalyst to percolate downward through the cellulosic biomass solids. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least about 250° C. in the presence of molecular hydrogen and the slurry catalyst. Further details regarding lignin depolymerization and the use of viscosity monitoring as a means of process control are described in commonly owned U.S. Patent Application 61/720,765, filed Oct. 31, 2012 and incorporated herein by reference in its entirety.

After forming the alcoholic component from the cellulosic biomass solids, at least a portion of the alcoholic component may be separated from the cellulosic biomass solids and further processed by performing a condensation reaction thereon, as generally described above. Processing of the alcoholic component that has partitioned between various liquid phases may take place with the phases separated from one another, or with the liquid phases mixed together. For example, in some embodiments, the alcoholic component in a fluid phase digestion medium may be processed separately from a light organics phase. In other embodiments, the light organics phase may be processed concurrently with the fluid phase digestion medium.

Optionally, the fluid phase digestion medium containing the alcoholic component may be subjected to a second catalytic reduction reaction external to the cellulosic biomass solids, if needed, for example, to increase the amount of soluble carbohydrates that are converted into the alcoholic component and/or to further reduce the degree of oxygenation of the alcoholic components that are formed. For example, in some embodiments, a glycol or more highly oxygenated alcohol may be transformed into a monohydric alcohol by performing a second catalytic reduction reaction. The choice of whether to perform a condensation reaction on a monohydric alcohol or a glycol may be based on a number of factors, as discussed in more detail below, and each approach may present particular advantages.

In some embodiments, a glycol produced from the cellulosic biomass solids may be fed to the condensation catalyst. Although glycols may be prone to coking when used in conjunction with condensation catalysts, particularly zeolite catalysts, the present inventors found the degree of coking to be manageable in the production of higher molecular weight compounds. Approaches for producing glycols from cellulosic biomass solids and feeding the glycols to a condensation catalyst are described in commonly owned U.S. Patent Application 61/720,704, filed Oct. 31, 2012 and incorporated herein by reference in its entirety. A primary advantage of feeding glycols to a condensation catalyst is that removal of water from glycols is considerably easier than from monohydric alcohols. Excessive water exposure can be particularly detrimental for zeolite catalysts and shorten their lifetime. Although monohydric alcohols are typically a preferred substrate for zeolite catalysts, they may be difficult to prepare in dried form due to azeotrope formation with water. Glycols, in contrast, are not believed to readily form binary azeotropes with water and may be produced in dried form by distillation.

In some embodiments, a dried alcoholic component, particularly a dried glycol, may be produced from cellulosic biomass solids and fed to a condensation catalyst. As used herein, the term "dried alcoholic component" refers to a fluid phase containing an alcoholic component that has had a least a portion of the water removed therefrom. Likewise, the terms "dried glycol" and "dried monohydric alcohol" respectively refer to a glycol or a monohydric alcohol that has had at least a portion of the water removed therefrom. It is to be recognized that a dried alcoholic component need not necessarily be completely anhydrous when dried, simply that its water content be reduced (e.g., less than 50 wt. % water). In some embodiments, the dried alcoholic component may comprise about 40 wt. % or less water. In some or other embodiments, the dried alcoholic component may comprise about 35 wt. % or less water, or about 30 wt. % or less water, or about 25 wt. % or less water, or about 20 wt. % or less water, or about 15 wt. % or less water, or about 10 wt. % or less water, or about 5 wt. % or less water. In some embodiments of the methods described herein, a substantially anhydrous alcoholic component may be produced upon drying. As used herein, a substance will be considered to be substantially anhydrous if it contains about 5 wt. % water or less.

In other embodiments, it may be more desirable to feed monohydric alcohols to the condensation catalyst due to a lower incidence of coking. As previously described, monohydric alcohols may be more difficult to produce in dried form due to azeotrope formation during distillation. In some embodiments, monohydric alcohols produced from cellulosic biomass solids may be fed directly to a condensation catalyst, without drying. In other embodiments, dried monohydric alcohols may be fed to a condensation catalyst. In some embodiments, dried monohydric alcohols may be produced from dried glycols. Specifically, dried glycols may be produced as described hereinabove, and the dried glycols may then be subjected to a catalytic reduction reaction to produce monohydric alcohols. The monohydric alcohols may contain a comparable amount of water to that present in the dried glycols from which they were formed. Thus, forming dried monohydric alcohols in the foregoing manner may desirably allow a reduced incidence of coking to be realized while maintaining lifetime of the condensation catalyst by providing a dried feed. The foregoing approach for producing dried monohydric alcohols from cellulosic biomass solids is described in commonly owned U.S. Patent Application 61/720,714, filed Oct. 31, 2012 and incorporated herein by reference in its entirety.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of dried glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

Various techniques for processing a phenolics liquid phase produced from cellulosic biomass solids are described in commonly owned U.S. Patent Applications 61/720,689, 61/720,747, and 61/720,774, each filed on Oct. 31, 2012 and incorporated herein by reference in its entirety. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom. The catalyst may then be regenerated, returned to the cellulosic biomass solids, or any combination thereof.

In some embodiments, heating of the cellulosic biomass solids and the fluid phase digestion medium to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least about 30 bar. In some embodiments, heating the cellulosic biomass solids and the fluid phase digestion medium may take place at a pressure of at least about 60 bar, or at a pressure of at least about 90 bar. In some embodiments, heating the cellulosic biomass solids and the fluid phase digestion medium may take place at a pressure ranging between about 30 bar and about 430 bar. In some embodiments, heating the cellulosic biomass solids and the fluid phase digestion medium may take place at a pressure ranging between about 50 bar and about 330 bar, or at a pressure ranging between about 70 bar and about 130 bar, or at a pressure ranging between about 30 bar and about 130 bar.

To facilitate a better understanding of the present invention, the following examples of preferred embodiments are given. In no way should the following examples be read to limit, or to define, the scope of the invention.

EXAMPLES

Example 1

Hydrothermal Digestion of Pine Softwood Minichips

A 100 mL Parr reactor was charged with 60 grams of 35% ethanol in deionized water solvent, 0.19 grams of potassium carbonate buffer, and 1.8 grams of slurry catalyst. The slurry catalyst was a sulfided nickel oxide promoted cobalt molybdate catalyst (DC-2534, Criterion Catalyst & Technologies L.P., containing 1-10% cobalt oxide and molybdenum trioxide (up to 30 wt %) on alumina, and less than 2% nickel), which was previously sulfided as described in United States Patent Application Publication 2010/0236988, incorporated herein by reference in its entirety. 6 grams of pine softwood minichips having nomimal dimensions of 3 mm×4 mm×5 mm were then added to the reactor, which was then pressurized with 55 bar of hydrogen. The reactor was then heated at 190° C. for 1 hour, followed by heating at 250° C. for 4 hours. Thereafter, the reactor was cooled, and 6 grams of liquid product were removed by a 0.5 micron filtered dip tube. The reactor was then repressurized as above, and 8 subsequent cycles of heating and liquid product withdrawal were conducted. The final liquid product contained $C_3$-$C_6$ mono-oxygenated hydrocarbons and $C_2$-$C_3$ glycols. Residual ethanol and water were also present.

Example 2

Lateral Disposition of Pine Softwood Minichips 160 mL of pine softwood minichips (39% moisture) having nominal dimensions of 3 mm×5 mm×5 mm were poured from a beaker over a distance of 25 cm onto a 20.25 cm diameter polyethylene plate. The pile of chips assumed an angle of repose of 55 degrees. A bottom base of 8.25 cm was obtained.

Example 3

Lateral Disposition of Steamed Pine Softwood Minichips

Example 2 was repeated, except that the minichips were saturated with steam to 60% moisture. In this case, the angle of repose was about 50 degrees, and the bottom base was 9 cm.

Example 4

Lateral Disposition of Steam Pine Softwood Minichips in Water

Example 3 was repeated with dropping of the minichips from the same elevation into a polyethylene bucket of the same 20.25 cm diameter filled with 15.25 cm of water. About 10% of the minichips dispersed along the entirety of the water surface, and the majority sank in the water. For the sunken minichips, the angle of repose was about 30 degrees, and the bottom base was 11 cm and 2.5 cm high. This represents more than a 150% increase in the area of minichip distribution compared to that obtained in the absence of a solvent.

Therefore, present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

We claim:

1. A method comprising:
providing a hydrothermal digestion unit having a length or a width that is greater than its height, the hydrothermal digestion unit containing a fluid phase digestion medium and a slurry catalyst capable of activating molecular hydrogen;
introducing cellulosic biomass solids to the hydrothermal digestion unit;
distributing the cellulosic biomass solids laterally within the hydrothermal digestion unit, the fluid phase digestion medium at least partially covering the cellulosic biomass solids after they have been distributed;
after or while the cellulosic biomass solids are being distributed, supplying an upwardly directed flow of molecular hydrogen through the cellulosic biomass solids and the fluid phase digestion medium; and
heating the cellulosic biomass solids in the presence of the slurry catalyst and the molecular hydrogen, thereby forming an alcoholic component derived from the cellulosic biomass solids.

2. The method of claim 1, wherein the upwardly directed flow of molecular hydrogen at least partially distributes the slurry catalyst in the cellulosic biomass solids.

3. The method of claim 1, wherein the cellulosic biomass solids are distributed laterally within the hydrothermal digestion unit by floating the cellulosic biomass solids on the fluid phase digestion medium.

4. The method of claim 1, wherein the cellulosic biomass solids are introduced to the hydrothermal digestion unit at a plurality of locations disposed laterally about an upper surface of the hydrothermal digestion unit.

5. The method of claim 1, wherein the cellulosic biomass solids are distributed laterally within the hydrothermal digestion unit by a solids transport mechanism located therein.

6. The method of claim 5, wherein the solids transport mechanism comprises a screw impeller.

7. The method of claim 1, wherein the cellulosic biomass solids are distributed laterally within the hydrothermal digestion unit by circulating the fluid phase digestion medium and the slurry catalyst laterally therethrough.

8. The method of claim 1, further comprising:
removing at least a portion of the fluid phase digestion medium and the slurry catalyst from the hydrothermal digestion unit, after the alcoholic component has been formed.

9. The method of claim 8, further comprising:
returning at least a portion of the fluid phase digestion medium and the slurry catalyst to the hydrothermal digestion unit; and
circulating at least a portion of the fluid phase digestion medium and the slurry catalyst laterally through the hydrothermal digestion unit.

10. The method of claim 9, wherein the fluid phase digestion medium and the slurry catalyst are circulated laterally through the hydrothermal digestion unit in the same direction in which the cellulosic biomass solids are being distributed in the hydrothermal digestion unit.

11. The method of claim 1, further comprising:
recirculating at least a portion of the molecular hydrogen from a headspace of the hydrothermal digestion unit to a source of the upwardly directed flow of molecular hydrogen.

12. The method of claim 1, wherein the fluid phase digestion medium comprises an organic solvent and water.

13. The method of claim 1, wherein the slurry catalyst comprises a poison-tolerant catalyst.

14. The method of claim 13, wherein the poison-tolerant catalyst comprises a sulfided catalyst.

15. A method comprising:
providing a first hydrothermal digestion unit having a length or a width that is greater than its height, the first hydrothermal digestion unit containing a fluid phase digestion medium and a slurry catalyst capable of activating molecular hydrogen;
introducing cellulosic biomass solids to the first hydrothermal digestion unit;
distributing the cellulosic biomass solids laterally within the first hydrothermal digestion unit, the fluid phase digestion medium at least partially covering the cellulosic biomass solids after they have been distributed;
after or while the cellulosic biomass solids are being distributed, supplying an upwardly directed flow of molecular hydrogen through the cellulosic biomass solids and the fluid phase digestion medium in the first hydrothermal digestion unit;
heating the cellulosic biomass solids in the presence of the slurry catalyst and the molecular hydrogen in the first hydrothermal digestion unit, thereby forming partially digested cellulosic biomass solids and an alcoholic component derived from the cellulosic biomass solids;
transferring the partially digested cellulosic biomass solids, the fluid phase digestion medium, and the slurry catalyst to a second hydrothermal digestion unit, the second hydrothermal digestion unit being fluidly coupled to the first hydrothermal digestion unit;
supplying an upwardly directed flow of molecular hydrogen through the partially digested cellulosic biomass solids and the fluid phase digestion medium in the second hydrothermal digestion unit; and
heating the partially digested cellulosic biomass solids in the presence of the slurry catalyst and the molecular hydrogen in the second hydrothermal digestion unit, thereby further forming the alcoholic component.

16. The method of claim 15, wherein the upwardly directed flow of molecular hydrogen at least partially distributes the slurry catalyst in the cellulosic biomass solids or partially digested cellulosic biomass solids.

17. The method of claim 15, wherein the second hydrothermal digestion unit has a height that is greater than its length or its width.

18. The method of claim 17, wherein the bottom of the first hydrothermal digestion unit is fluidly coupled to the top of the second hydrothermal digestion unit.

19. The method of claim 15, wherein the second hydrothermal digestion unit has a length or a width that is greater than its height.

20. The method of claim 19, wherein the first hydrothermal digestion unit and the second hydrothermal digestion unit are fluidly coupled to one another end-to-end.

21. The method of claim 19, wherein the bottom of the first hydrothermal digestion unit is fluidly coupled to the top of the second hydrothermal digestion unit.

22. The method of claim 15, further comprising:
removing at least a portion of the fluid phase digestion medium and the slurry catalyst from the second hydrothermal digestion unit, after the alcoholic component has been formed.

23. The method of claim 22, further comprising:
returning at least a portion of the fluid phase digestion medium and the slurry catalyst to the first hydrothermal digestion unit; and
circulating at least a portion of the fluid phase digestion medium and the slurry catalyst laterally through the first hydrothermal digestion unit.

24. The method of claim 15, wherein the cellulosic biomass solids are introduced to the first hydrothermal digestion unit at a plurality of locations disposed laterally about an upper surface of the first hydrothermal digestion unit.

25. The method of claim 15, wherein the cellulosic biomass solids are distributed laterally within the first hydrothermal digestion unit by floating the cellulosic biomass solids on the fluid phase digestion medium.

26. The method of claim 15, wherein the cellulosic biomass solids are distributed laterally within the first hydrothermal digestion unit by a solids transport mechanism located therein.

27. The method of claim 26, wherein the solids transport mechanism comprises a screw impeller.

28. The method of claim 15, wherein the cellulosic biomass solids are distributed laterally within the first hydrothermal digestion unit by circulating the fluid phase digestion medium and the slurry catalyst laterally therethrough.

29. The method of claim 28, wherein the fluid phase digestion medium and the slurry catalyst are circulated from the second hydrothermal digestion unit to the first hydrothermal digestion unit.

30. The method of claim 15, further comprising:
recirculating at least a portion of the molecular hydrogen from a headspace of either hydrothermal digestion unit to the same hydrothermal digestion unit or a different hydrothermal digestion unit, the molecular hydrogen being recirculated to a source of the upwardly directed flow of molecular hydrogen therein.

31. The method of claim 15, wherein the fluid phase digestion medium comprises an organic solvent and water.

32. The method of claim 15, wherein the slurry catalyst comprises a poison-tolerant catalyst.

33. The method of claim 32, wherein the poison-tolerant catalyst comprises a sulfided catalyst.

* * * * *